United States Patent
Skiba et al.

(10) Patent No.: US 10,406,347 B2
(45) Date of Patent: Sep. 10, 2019

(54) METHODS AND DEVICES FOR WOUND THERAPY

(71) Applicant: VOMARIS INNOVATIONS, INC., Tempe, AZ (US)

(72) Inventors: Jeffry Skiba, Chandler, AZ (US); Inder Raj S. Makin, Tempe, AZ (US)

(73) Assignee: Vomaris Innovations, Inc., Chandler, AZ (US)

( * ) Notice: Subject to any disclaimer, the term of this patent is extended or adjusted under 35 U.S.C. 154(b) by 837 days.

(21) Appl. No.: 14/888,264

(22) PCT Filed: Mar. 3, 2014

(86) PCT No.: PCT/US2014/019974
§ 371 (c)(1),
(2) Date: Oct. 30, 2015

(87) PCT Pub. No.: WO2014/178944
PCT Pub. Date: Nov. 6, 2014

(65) Prior Publication Data
US 2016/0059009 A1     Mar. 3, 2016

Related U.S. Application Data

(60) Provisional application No. 61/818,797, filed on May 2, 2013, provisional application No. 61/821,362, filed (Continued)

(51) Int. Cl.
*A61N 1/04*     (2006.01)
*A61F 13/00*    (2006.01)
(Continued)

(52) U.S. Cl.
CPC ...... *A61N 1/0468* (2013.01); *A61F 13/00038* (2013.01); *A61F 13/00051* (2013.01); (Continued)

(58) Field of Classification Search
CPC .. A61N 1/0428; A61N 1/0464; A61N 1/0468; A61N 1/0476; A61N 1/0492;
(Continued)

(56) References Cited

U.S. PATENT DOCUMENTS 5,578,022 A * 11/1996 Scherson .......... A61F 13/00068
  604/304
7,457,667 B2 * 11/2008 Skiba ..................... A61N 1/303
  600/372
(Continued)

FOREIGN PATENT DOCUMENTS

WO     2014/178944 A1    11/2014

OTHER PUBLICATIONS

International Search Report of PCT/US2014/01944, dated Jul. 1, 2014.
(Continued)

*Primary Examiner* — Keri J Nelson
(74) *Attorney, Agent, or Firm* — K&L Gates LLP; Louis C. Cullman; Hal Gibson

(57) ABSTRACT

A system for wound treatment includes adjunctive wound therapy devices and substrates comprising multiple first reservoirs and multiple second reservoirs. Selected ones of the multiple first reservoirs include a reducing agent, and first reservoir surfaces of selected ones of the multiple first reservoirs are proximate to a first substrate surface. Selected ones of the multiple second reservoirs include an oxidizing agent, and second reservoir surfaces of selected ones of the multiple second reservoirs are proximate to the first substrate surface.

14 Claims, 3 Drawing Sheets

Related U.S. Application Data on May 9, 2013, provisional application No. 61/821,365, filed on May 9, 2013.

(51) Int. Cl.

| | | |
|---|---|---|
| *A61M 1/00* | (2006.01) | |
| *A61M 35/00* | (2006.01) | |
| *A61N 1/30* | (2006.01) | |
| *A61N 1/32* | (2006.01) | |
| *A61G 10/02* | (2006.01) | |
| *A61F 13/02* | (2006.01) | |
| *A61N 1/20* | (2006.01) | |

(52) U.S. Cl.
CPC ........ *A61F 13/00063* (2013.01); *A61F 13/02* (2013.01); *A61G 10/026* (2013.01); *A61M 1/0088* (2013.01); *A61M 35/00* (2013.01); *A61N 1/0428* (2013.01); *A61N 1/0464* (2013.01); *A61N 1/0476* (2013.01); *A61N 1/0492* (2013.01); *A61N 1/205* (2013.01); *A61N 1/30* (2013.01); *A61N 1/325* (2013.01); *A61N 1/326* (2013.01); *A61F 2013/0028* (2013.01); *A61M 2202/0208* (2013.01)

(58) Field of Classification Search
CPC .......... A61N 1/205; A61N 1/30; A61N 1/325; A61N 1/326; A61F 13/00038; A61F 13/00051; A61F 13/00063; A61F 13/00068; A61M 1/0088; A61M 35/00
USPC ..................................... 602/2, 41–43, 48, 53
See application file for complete search history.

(56) References Cited

U.S. PATENT DOCUMENTS

| | | | |
|---|---|---|---|
| 7,672,719 B2 * | 3/2010 | Skiba | A61N 1/303 |
| | | | 607/1 |
| 7,857,806 B2 | 12/2010 | Karpowicz et al. | |
| 8,287,475 B2 | 10/2012 | Smithers et al. | |
| 2010/0204752 A1 * | 8/2010 | Tremblay | A61N 1/205 |
| | | | 607/50 |
| 2010/0312293 A1 | 12/2010 | Skiba | |
| 2011/0060204 A1 | 3/2011 | Weston | |
| 2012/0157750 A1 | 6/2012 | Robinson et al. | |

OTHER PUBLICATIONS

International Search Report for International Application No. PCT/US2014/019974 filed on Mar. 3, 2014.
Written Opinion for International Application No. PCT/US2014/019974 filed on Mar. 3, 2014.
Supplementary European Search Report for European Patent Application 14791377.6 dated Nov. 30, 2016.

* cited by examiner

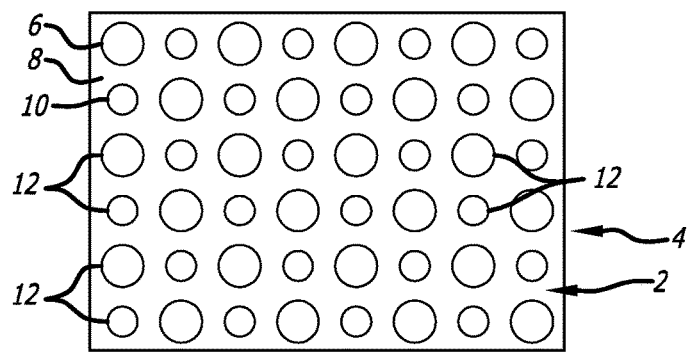
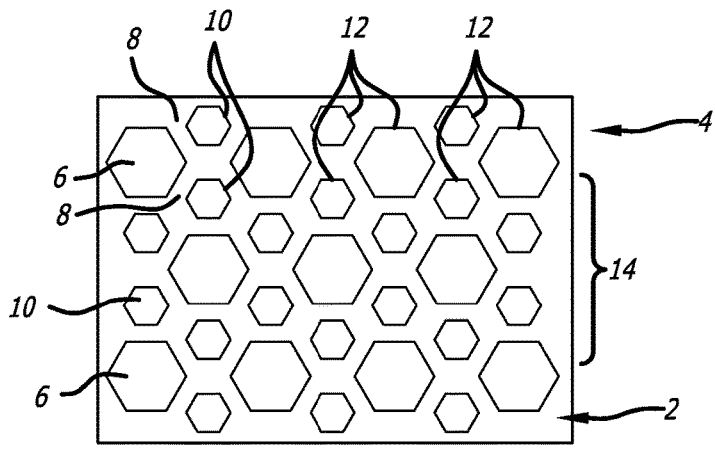
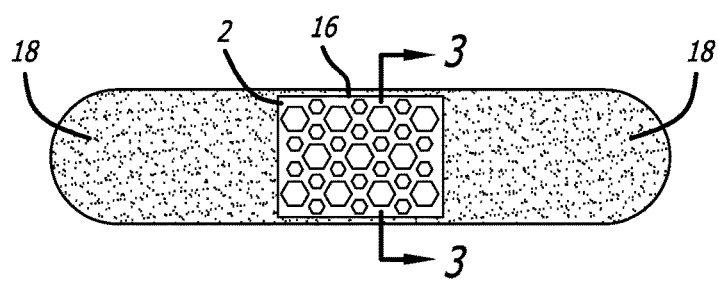
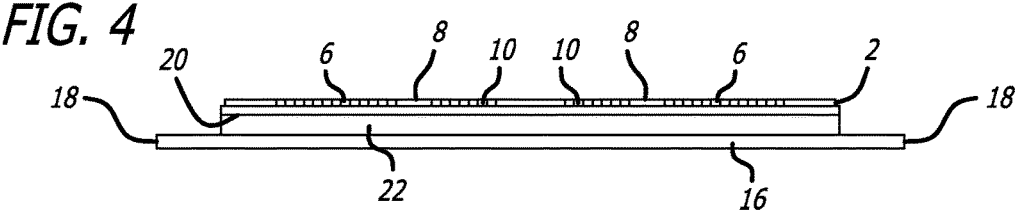

METHODS AND DEVICES FOR WOUND THERAPY

CROSS REFERENCE TO RELATED APPLICATIONS

This application is a national phase of PCT/US2014/019974 filed on Mar. 3, 2014 which claims priority to U.S. Provisional Patent Application Nos. 61/818,797 filed May 2, 2013, 61/821,362, filed May 9, 2013, and 61/821,365, filed May 9, 2013, each of which are incorporated by reference herein in their entireties.

FIELD

Biologic tissues and cells, microbes, bacteria, viruses, fungi, and other organisms or organic matter can be affected by electrical stimulus. Accordingly, apparatus and techniques for applying electric stimulus to organic matter have been developed to address a number of medical issues. These apparatus and techniques can include methods, devices, and systems for applying adjunctive wound therapies, such as Negative Pressure Wound Therapy (NPWT), Topical Oxygen Therapy (TOT), Hyperbaric Oxygen Therapy (HBOT), Multi-Layer Compression Therapy (MLCT), or other adjunctive wound therapies. The present specification relates to methods and devices useful for healing wounds, directing cell migration, increasing cell nutrient uptake, promoting wound healing, reducing inflammation, and providing antibacterial effects.

SUMMARY

Aspects disclosed herein comprise bioelectric devices that comprise a multi-array matrix of biocompatible microcells. Such matrices can include a first array comprising a pattern of microcells formed from a first conductive solution, the solution including a metal species; and a second array comprising a pattern of microcells formed from a second conductive solution, the solution including a metal species capable of defining at least one voltaic cell for spontaneously generating at least one electrical current with the metal species of the first array when said first and second arrays are introduced to an electrolytic solution and said first and second arrays are not in physical contact with each other. Certain aspects utilize an external power source such as AC or DC power or pulsed RF or pulsed current, such as high voltage pulsed current. In one embodiment, the electrical energy is derived from the dissimilar metals creating a battery at each cell/cell interface, whereas those embodiments with an external power source may require conductive electrodes in a spaced apart configuration to predetermine the electric field shape and strength. The external source could provide energy for a longer period than the batteries on the surface.

The devices can also generate a localized electric field in a pattern determined by the distance and physical orientation of the cells or electrodes. Effective depth of the electric field can be predetermined by the orientation and distance of the cells or electrodes. In aspects the devices can be coated either totally or partially with a hydrogel, or glucose or any other drug, cellular nutrition, stem cells, or other biologic. In embodiments the electric field can be extended, for example through the use of a hydrogel. In certain embodiments, for example treatment methods, it can be preferable to utilize AC or DC current.

Further aspects include a method of directing cell migration using a device disclosed herein. These aspects include methods of improving re-epithelialization.

Further aspects include methods of increasing glucose uptake as well as methods of increasing cellular thiol levels. Additional aspects include a method of energizing mitochondria.

Further aspects include a method of stimulating cellular protein expression.

Further aspects include a method of stimulating cellular DNA synthesis.

Further aspects include a method of stimulating cellular $Ca^{2+}$ uptake.

Other embodiments include devices and methods for increasing capillary density.

Embodiments include devices and methods for increasing transcutaneous partial pressure of oxygen. Further embodiments include methods and devices for treating or preventing pressure ulcers.

Additional aspects include a method of preventing bacterial biofilm formation. Aspects also include a method of reducing microbial or bacterial proliferation, killing microbes or bacteria, killing bacteria through a biofilm layer, or preventing the formation of a biofilm. Embodiments include methods using devices disclosed herein in combination with antibiotics for reducing microbial or bacterial proliferation, killing microbes or bacteria, killing bacteria through a biofilm layer, or preventing the formation of a biofilm.

Further aspects include methods of treating diseases related to metabolic deficiencies, such as diabetes, or other disease wherein the patient exhibits a compromised metabolic status.

Additional aspects disclosed herein include a method for treating a wound comprising securing a wound management system in a sealed environment adjacent the wound and maintaining negative pressure in the sealed environment, wherein such wound management system comprises a pliable dressing material comprising on its surface a multi-array matrix of biocompatible microcells. In an aspect the matrix comprises a first array forming a pattern of microcells formed from a first conductive solution, such conductive solution including a metal species and a second array forming a pattern of microcells formed from a second conductive solution, such conductive solution including a metal species capable of defining at least one voltaic cell for spontaneously generating at least one electrical current with the metal species of the first array when said first and second arrays are introduced to an electrolytic solution and said first and second arrays are not in physical contact with each other. Further aspects can include imaging a wound in three dimensions.

Also disclosed is a system for providing topical oxygen therapy to a wound, the system comprising a device for providing a source of oxygen and a wound management system comprising a pliable dressing material comprising a surface having a multi-array matrix of biocompatible microcells. In aspects the matrix comprises a first array comprising a pattern of microcells formed from a first conductive metal solution, such conductive metal solution including a metal species and a second array comprising a pattern of microcells formed from a second conductive metal solution, such conductive metal solution including a metal species capable of defining at least one voltaic cell for generating at least one electrical field with the metal species of the first array when said first and second arrays are introduced to an electrolytic solution and said first and second arrays are not in physical contact with each other. Also disclosed is a conduit configured to communicate oxygen from the device to the wound management system. In an aspect the pliable dressing material is shaped to fit the wound. An aspect disclosed includes applying hydrogel to the wound.

Further aspects include a method for treating a wound comprising securing a wound management system in a sealed environment adjacent the wound and maintaining an increased oxygen concentration in the sealed environment, wherein such wound management system comprises a pliable dressing material comprising on its surface a multi-array matrix of biocompatible microcells.

In certain aspects the matrix comprises a first array comprising a pattern of microcells formed from a first conductive metal solution, such conductive metal solution including a metal species and a second array comprising a pattern of microcells formed from a second conductive metal solution, such conductive metal solution including a metal species capable of defining at least one voltaic cell for spontaneously generating at least one electrical field with the metal species of the first array when the first and second arrays are introduced to an electrolytic solution and the first and second arrays are not in physical contact with each other. Further aspects include the application of an adenosine-5'-triphosphate (ATP) source to the wound.

BRIEF DESCRIPTION OF THE DRAWINGS

FIG. 1 is a detailed plan view of an embodiment disclosed herein.

FIG. 2 is a detailed plan view of a pattern of applied electrical conductors in accordance with an embodiment disclosed herein.

FIG. 3 is an adhesive bandage using the applied pattern of FIG. 2.

FIG. 4 is a cross-section of FIG. 3 through line 3-3.

DETAILED DESCRIPTION

Figure 5:
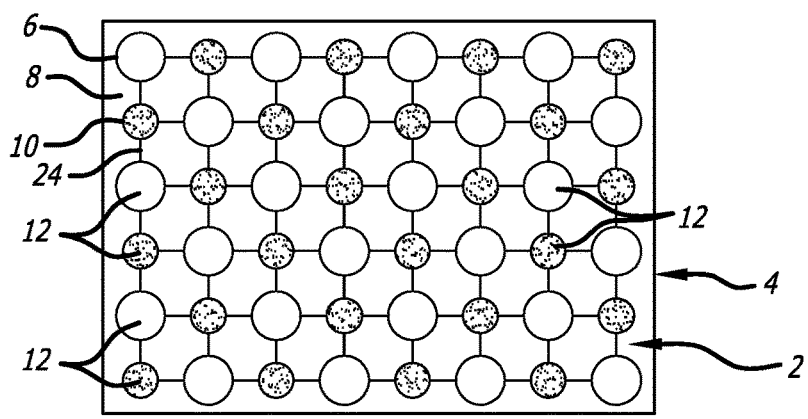
FIG. 5 is a detailed plan view of an alternate embodiment disclosed herein which includes fine lines of conductive metal solution connecting electrodes.

Embodiments disclosed herein include systems that can provide a low level electric field (LLEF) to a tissue or organism (thus a "LLEF system") or, when brought into contact with an electrically conducting material, can provide a low level micro-current (LLMC) to a tissue or organism (thus a "LLMC system"). Thus, in embodiments a LLMC system is a LLEF system that is in contact with an electrically conducting material. In certain embodiments, the micro-current or electric field can be modulated, for example, to alter the duration, size, shape, field depth, current, polarity, or voltage of the system. In embodiments the watt-density of the system can be modulated.

Embodiments disclosed herein comprise patterns of microcells. The patterns can be designed to produce an electric field, an electric current, or both over living cells. In embodiments the pattern can be designed to produce a specific size, strength, density, shape, or duration of electric field or electric current. In embodiments reservoir or dot size and separation can be altered.

In embodiments devices disclosed herein can apply an electric field, an electric current, or both wherein the field, current, or both can be of varying size, strength, density, shape, or duration in different areas of a wound or tissue. In embodiments, by micro-sizing the electrodes or reservoirs, the shapes of the electric field, electric current, or both can be customized, increasing or decreasing very localized watt densities and allowing for the design of "smart patterned electrodes" where the amount of e field over a tissue can be designed or produced or adjusted based on feedback from the tissue or on an algorithm within the sensors and fedback to a control module. The electric field, electric current, or both can be strong in one zone and weaker in another. The electric field, electric current, or both can change with time and be modulated based on treatment goals or feedback from the tissue or patient. The control module can monitor and adjust the size, strength, density, shape, or duration of electric field or electric current based on tissue parameters.

A dressing over tissue such as a joint in motion can move relative to the tissue. Reducing the amount of motion between tissue and dressing can be advantages to healing. In embodiments, traction or friction blisters can be treated, minimized, or prevented. Slotting or placing strategic cuts into the dressing can make less friction on the wound. In embodiments, use of an elastic dressing similar to the elasticity of the skin is also possible. The use of the dressing as a temporary bridge to reduce stress across the wound site can reduce stress at the sutures or staples and this will reduce scarring and encourage healing.

The devices can be used to modulate cell characteristics, such as for example to direct and promote cell migration or infiltration, or to increase uptake of materials such as glucose, or to increase cell signaling activity or to defeat bacterial signaling such as quorum sensing. The devices can be used therapeutically, such as to promote the healing of wounds, or in the treatment of disease such as those related to metabolic deficiencies, such as diabetes. Further disclosure relating to the use of electrical current to heal wounds can be found in U.S. Pat. No. 7,457,667 entitled CURRENT PRODUCING SURFACE FOR A WOUND DRESSING issued Nov. 25, 2008, which is incorporated herein by reference in its entirety.

Embodiments disclosed herein comprise biocompatible electrodes or reservoirs or dots on a surface, for example a fabric or the like. In embodiments the surface can be pliable. In embodiments the surface can comprise a gauze or mesh. Suitable types of pliable surfaces for use in embodiments disclosed herein can be absorbent textiles, low-adhesives, vapor permeable films, hydrocolloids, hydrogels, alginates, foams, foam-based materials, cellulose-based materials including Kettenbach fibers, hollow tubes, fibrous materials, such as those impregnated with anhydrous/hygroscopic materials, beads and the like, or any suitable material as known in the art. In embodiments the pliable material can form, for example, a bandage, a wrist band, a neck band, a waist band, a wound dressing, cloth, fabric, or the like. Embodiments can include coatings on the surface, such as, for example, over or between the electrodes. Such coatings can include, for example, silicone, and electrolytic mixture, hypoallergenic agents, drugs, biologics, stem cells, skin substitutes or the like. Drugs suitable for use with embodiments of the invention include analgesics, antibiotics, anti-inflammatories, or the like. In embodiments the electric field or current produced can "drive" the drug through the skin or surface tissue.

In embodiments the material can include a port to access the interior of the material, for example to add fluid, gel, or some other material to the dressing. Certain embodiments can comprise a "blister" top that can enclose a material. In embodiments the blister top can contain a material that is released into the dressing when the blister is pressed, for example a liquid.

In embodiments the system comprises a component such as elastic to maintain or help maintain its position. In embodiments the system comprises a component such as an adhesive to maintain or help maintain its position. The adhesive component can be covered with a protective layer that is removed to expose the adhesive at the time of use. In embodiments the adhesive can comprise, for example, sealants, such as hypoallergenic sealants, gecko sealants, mussel sealants, waterproof sealants such as epoxies, and the like.

In embodiments the positioning component can comprise an elastic film with an elasticity, for example, similar to that of skin, or greater than that of skin, or less than that of skin. In embodiments, the LLMC or LLEF system can comprise a laminate where layers of the laminate can be of varying elasticities. For example, an outer layer may be highly elastic and an inner layers in-elastic. The in-elastic layer can be made to stretch by placing stress relieving discontinuous regions or slits through the thickness of the material so there is a mechanical displacement rather than stress that would break the fabric weave before stretching would occur. In embodiments the slits can extend completely through a layer or the system or can be placed where expansion is required. In embodiments of the system the slits do not extend all the way through the system or a portion of the system such as the dressing material. In embodiments the discontinuous regions can pass halfway through the long axis of the wound management system.

In certain embodiments the surface can comprise the surface of, for example, a catheter, or a microparticle. Such embodiments can be used to treat a subject internally both locally or systemically. For example, the microparticles can be used to make a pharmaceutical composition in combination with a suitable carrier. In embodiments nanotechnology such as nanobots can be used to provide LLMC systems that can be used as components of pharmaceutical formulations, such as injected, inhaled, or orally administered formulations.

"Activation gel" as used herein means a composition useful for maintaining a moist environment about the wound or promoting healing within and about the wound.

"Adjunctive therapies" as used herein means therapies used in combination with a wound healing device disclosed herein. Such therapies can include, for example, NPWT, HBOT, TOT, MLCT, or other therapies useful in wound healing.

"Affixing" as used herein can mean contacting a patient or tissue with a device or system disclosed herein.

"Applied" or "apply" as used herein refers to contacting a surface with a conductive material, for example printing, painting, or spraying a conductive ink on a surface. Alternatively, "applying" can mean contacting a patient or tissue or organism with a device or system disclosed herein.

"Cell infiltration" as used herein refers to cell migration to a target tissue or area to which cell migration is desired, for example a wound.

"Conductive material" as used herein refers to an object or type of material which permits the flow of electric charge in one or more directions. Conductive materials can include solids such as metals or carbon, or liquids such as conductive metal solutions and conductive gels. Conductive materials can be applied to form at least one matrix. Conductive liquids can dry, cure, or harden after application to form a solid material.

"Discontinuous region" as used herein refers to a "void" in a material such as a hole, slot, slit, or the like. The term can mean any void in the material though typically the void is of a regular shape. The void in the material can be entirely within the perimeter of a material or it can extend to the perimeter of a material.

"Dots" as used herein refers to discrete deposits of dissimilar reservoirs that can function as at least one battery cell. The term can refer to a deposit of any suitable size or shape, such as squares, circles, triangles, lines, etc. The term can be used synonymously with, microcells, etc.

"Electrode" refers to similar or dissimilar conductive materials. In embodiments utilizing an external power source the electrodes can comprise similar conductive materials. In embodiments that do not use an external power source, the electrodes can comprise dissimilar conductive materials that can define an anode and a cathode.

"Expandable" as used herein refers to the ability to stretch while retaining structural integrity and not tearing. The term can refer to solid regions as well as discontinuous or void regions; solid regions as well as void regions can stretch or expand.

"Galvanic cell" as used herein refers to an electrochemical cell with a positive cell potential, which can allow chemical energy to be converted into electrical energy. More particularly, a galvanic cell can include a first reservoir serving as an anode and a second, dissimilar reservoir serving as a cathode. Each galvanic cell can store chemical potential energy. When a conductive material is located proximate to a cell such that the material can provide electrical and/or ionic communication between the cell elements the chemical potential energy can be released as electrical energy. Accordingly, each set of adjacent, dissimilar reservoirs can function as a single-cell battery, and the distribution of multiple sets of adjacent, dissimilar reservoirs within the apparatus can function as a field of single-cell batteries, which in the aggregate forms a multiple-cell battery distributed across a surface. In embodiments utilizing an external power source the galvanic cell can comprise electrodes connected to an external power source, for example a battery or other power source. In embodiments that are externally-powered, the electrodes need not comprise dissimilar materials, as the external power source can define the anode and cathode. In certain externally powered embodiments, the power source need not be physically connected to the device.

"Hyperbaric Oxygen Therapy" (HBOT) is the medical use of oxygen at a level higher than atmospheric pressure. Typically the equipment used to perform the procedure consists of a pressure chamber which may be of rigid or flexible construction and a means of delivering up to 100% oxygen. Operation is performed to a predetermined schedule by trained personnel who monitor the patient and can adjust the schedule as required. HBOT found early use in the treatment of decompression sickness, and has also shown great effectiveness in treating conditions such as gas gangrene and carbon monoxide poisoning. More recent research has examined the possibility that it may also have value for other conditions such as cerebral palsy and multiple sclerosis, but no significant evidence has been found.

"Matrix" or "matrices" as used herein refer to a pattern or patterns, such as those formed by electrodes on a surface. Matrices can be designed to vary the electric field or electric microcurrent generated. For example, the strength and shape of the field or microcurrent can be altered, or the matrices can be designed to produce an electric field(s) or current of a desired strength or shape.

"Multi-layered compression therapy" ("MLCT") as used herein refers to compression treatment of leg ulcers and other wounds using layers comprised of material with different elastic properties.

"Negative-pressure wound therapy" (NPWT) is a therapeutic technique using a vacuum dressing to promote healing in acute or chronic wounds and enhance healing of first and second degree burns. The therapy involves the controlled application of sub-atmospheric pressure to the local wound environment using a sealed wound dressing connected to a vacuum pump. NPWT promotes wound healing by applying a vacuum through a special sealed dressing. The continued vacuum draws out fluid from the wound and increases blood flow to the area. The vacuum can be applied continuously or intermittently, depending on the type of wound being treated and the clinical objectives. Typically, the dressing is changed two to three times per week. NPWT devices can allow delivery of fluids, such as saline or antibiotics to irrigate the wound, intermittent removal of used fluid supports the cleaning and drainage of the wound bed. General technique for NPWT is as follows: a dressing or filler material is fitted to the contours of a wound (which is covered with a non-adherent dressing film) and the overlying foam is then sealed with a transparent film. A drainage tube is connected to the dressing through an opening of the transparent film. A vacuum tube is connected through an opening in the film drape to a canister on the side of a vacuum pump or vacuum source, turning an open wound into a controlled closed wound while removing excess fluid from the wound bed to enhance circulation and remove wound fluids. This creates a moist healing environment and reduces edema.

"Reduction-oxidation reaction" or "redox reaction" as used herein refers to a reaction involving the transfer of one or more electrons from a reducing agent to an oxidizing agent. The term "reducing agent" can be defined in some embodiments as a reactant in a redox reaction, which donates electrons to a reduced species. A "reducing agent" is thereby oxidized in the reaction. The term "oxidizing agent" can be defined in some embodiments as a reactant in a redox reaction, which accepts electrons from the oxidized species. An "oxidizing agent" is thereby reduced in the reaction. In various embodiments a redox reaction produced between a first and second reservoir provides a current between the dissimilar reservoirs. The redox reactions can occur spontaneously when a conductive material is brought in proximity to first and second dissimilar reservoirs such that the conductive material provides a medium for electrical communication and/or ionic communication between the first and second dissimilar reservoirs. In other words, in an embodiment electrical currents can be produced between first and second dissimilar reservoirs without the use of an external battery or other power source (e.g., a direct current (DC) such as a battery or an alternating current (AC) power source such as a typical electric outlet). Accordingly, in various embodiments a system is provided which is "electrically self contained," and yet the system can be activated to produce electrical currents. The term "electrically self contained" can be defined in some embodiments as being capable of producing electricity (e.g., producing currents) without an external battery or power source. The term "activated" can be defined in some embodiments to refer to the production of electric current through the application of a radio signal of a given frequency or through ultrasound or through electromagnetic induction. In other embodiments, a system can be provided which includes an external battery or power source. For example, an AC power source can be of any wave form, such as a sine wave, a triangular wave, or a square wave. AC power can also be of any frequency such as for example 50 Hz or 60 HZ, or the like. AC power can also be of any voltage, such as for example 120 volts, or 220 volts, or the like. In embodiments an AC power source can be electronically modified, such as for example having the voltage reduced, prior to use.

"Skin substitute" as used herein refers to a heterogeneous group of wound coverage materials that aid in would closure and replace the functions of the skin, either temporarily or permanently, depending on the product characteristics. These substances are alternatives to the standard wound coverage in circumstances when standard therapies are not desirable.

"Stretchable" as used herein refers to the ability of embodiments that stretch without losing some or all of their structural integrity. That is, embodiments can stretch to accommodate irregular wound surfaces or surfaces wherein one portion of the surface can move relative to another portion of the surface.

"Topical oxygen therapy" or "TOT" refers to the direct application of oxygen to wounds.

"Wound" as used herein includes abrasions, surgical incisions, cuts, punctures, tears, sores, ulcers, blisters, burns, amputations, bites, and any other breach or disruption of superficial tissue such as the skin, mucus membranes, epithelial linings, etc. Disruptions can include inflamed areas, polyps, ulcers, etc. A scar is intended to include hypertrophic scars, keloids, or any healed wound tissue of the afflicted individual. Superficial tissues include those tissues not normally exposed in the absence of a wound or disruption, such as underlying muscle or connective tissue. A wound is not necessarily visible nor does it necessarily involve rupture of superficial tissue, for example a wound can comprise a bacterial infection. Wounds can include insect and animal bites from both venomous and non-venomous insects and animals.

LLMC/LLEF Systems—Methods of Manufacture

A LLMC or LLEF system disclosed herein can comprise "anchor" regions or "arms" to affix the system securely. The anchor regions or arms can anchor the LLMC system, such as for example to areas around a joint where motion is minimal or limited. For example, a LLMC system can be secured to a wound proximal to a joint, and the anchor regions of the system can extend to areas of minimal stress or movement to securely affix the system. Further, the LLMC system can reduce stress on the wound site by "countering" the physical stress caused by movement. For example, the wound management system can be pre-stressed or stretched prior to application such that it "pulls" or "holds" the wound perimeter together.

A LLMC or LLEF system disclosed herein can comprise reinforcing sections. In embodiments the reinforcing sections can comprise sections that span the length of the system. In embodiments a LLMC or LLEF system can comprise multiple reinforcing sections such as at least 1 reinforcing section, at least 2 reinforcing sections, at least 3 reinforcing sections, at least 4 reinforcing sections, at least 5 reinforcing sections, at least 6 reinforcing sections, or the like.

In embodiments the LLMC or LLEF system can comprise additional materials to aid in healing. These additional materials can comprise activation gels, rhPDGF (recombinant human platelet-derived growth factor) (RE- GRANEX®), Vibronectin:IGF complexes, CELLSPRAY (Clinical Cell Culture Pty. Ltd., Australia), RECELL® (Clinical Cell Culture Pty. Ltd., Australia), INTEGRA® dermal regeneration template (Integra Life Sciences, U.S.), BIOMEND® (Zimmer Dental Inc., U.S.), INFUSE® (Medtronic Sofamor Danek Inc., U.S.), ALLODERM® (LifeCell Corp. U.S.), CYMETRA® (LifeCell Corp. U.S.), SEPRAPACK® (Genzyme Corporation, U.S.), SEPRAMESH® (Genzyme Corporation, U.S.), SKINTEMP® (Human BioSciences Inc., U.S.), COSMODERM® (Inamed Corporation, U.S.), COSMOPLAST® (Inamed Corporation, U.S.), OP-1® (Stryker Corporation, U.S.), ISOLAGEN® (Fibrocell Technologies Inc., U.S.), CARTICEL® (Genzyme Corporation, U.S.), APLIGRAF® (Sandoz AG Corporation, Switzerland), DERMAGRAFT® (Smith & Nephew Wound Management Corporation, U.S.), TRANSCYTE® (Shire Regenerative Medicine Inc., U.S.), ORCEL® (Orcell LLPC Corporation, U.S.), EPICEL® (Genzyme Corporation, U.S.), and the like. In embodiments the additional materials can be, for example, TEGADERM® 91110 (3M Corporation, U.S.), MEPILEX® Normal Gel 0.9% Sodium chloride (Molnlycke Health Care AB, Sweden), HISPAGEL® (BASF Corporation, U.S.), LUBRIGEL® (Sheffield Laboratories Corporation, U.S.) or other compositions useful for maintaining a moist environment about a wound or for ease of removal of the LLMC or LLEF system. In certain embodiments additional materials that can be added to the LLMC or LLEF system can include for example, vesicular-based formulations such as hemoglobin vesicles. In certain embodiments liposome-based formulations can be used.

Embodiments can include devices in the form of a gel, such as, for example, a one- or two-component gel that is mixed on use. Embodiments can include devices in the form of a spray, for example, a one- or two-component spray that is mixed on use. Embodiments can include devices that are heat-activated.

In embodiments, the LLMC or LLEF system can comprise instructions or directions on how to place the system to maximize its performance.

Embodiments of the LLMC or LLEF system disclosed herein can comprise electrodes or microcells. Each electrode or microcell can be or include a conductive metal. In embodiments, the electrodes or microcells can comprise any electrically-conductive material, for example, an electrically conductive hydrogel, metals, electrolytes, superconductors, semiconductors, plasmas, and nonmetallic conductors such as graphite and conductive polymers. Electrically conductive metals can include silver, copper, gold, aluminum, molybdenum, zinc, lithium, tungsten, brass, carbon, nickel, iron, palladium, platinum, tin, bronze, carbon steel, lead, titanium, stainless steel, mercury, Fe/Cr alloys, and the like. The electrode can be coated or plated with a different metal such as aluminum, gold, platinum or silver.

In certain embodiments reservoir or electrode geometry can comprise circles, polygons, lines, zigzags, ovals, stars, or any suitable variety of shapes. This provides the ability to design/customize surface electric field shapes as well as depth of penetration.

Reservoir or dot sizes and concentrations can be of various sizes, as these variations can allow for changes in the properties of the electric field created by embodiments of the invention. Certain embodiments provide an electric field at about 1 Volt and then, under normal tissue loads with resistance of 100 k to 300K ohms, produce a current in the range of 10 microamperes. The electric field strength can be determined by calculating ½ the separation distance and applying it in the z-axis over the midpoint between the cell. This indicates the theoretical location of the highest strength field line.

In certain embodiments dissimilar metals can be used to create an electric field with a desired voltage. In certain embodiments the pattern of reservoirs can control the watt density and shape of the electric field.

In embodiments "ink" or "paint" can comprise any conductive solution suitable for forming an electrode on a surface, such as a conductive metal solution. In embodiments "printing" or "painted" can comprise any method of applying a conductive material such as a conductive liquid material to a material upon which a matrix is desired.

In embodiments printing devices can be used to produce LLMC or LLEF systems disclosed herein. For example, inkjet or "3D" printers can be used to produce embodiments.

In certain embodiments the binders or inks used to produce LLMC or LLEF systems disclosed herein can include, for example, poly cellulose inks, poly acrylic inks, poly urethane inks, silicone inks, and the like. In embodiments the type of ink used can determine the release rate of electrons from the reservoirs. In embodiments various materials can be added to the ink or binder such as, for example, conductive or resistive materials can be added to alter the shape or strength of the electric field. Other materials, such as silicon, can be added to enhance scar reduction. Such materials can also be added to the spaces between reservoirs.

Certain embodiments can utilize a power source to create the electric current, such as a battery or a microbattery. The power source can be any energy source capable of generating a current in the LLMC system and can include, for example, AC power, DC power, radio frequencies (RF) such as pulsed RF, induction, ultrasound, and the like.

Dissimilar metals used to make a LLMC or LLEF system disclosed herein can be silver and zinc, and the electrolytic solution can include sodium chloride in water. In certain embodiments the electrodes are applied onto a non-conductive surface to create a pattern, most preferably an array or multi-array of voltaic cells that do not spontaneously react until they contact an electrolytic solution, for example wound fluids including any physiological fluid, such as blood, sweat, lymph, etc. Sections of this description use the terms "printing" with "ink," but it is understood that the patterns may instead be "painted" with "paints." The use of any suitable means for applying a conductive material is contemplated. In embodiments "ink" or "paint" can comprise any solution suitable for forming an electrode on a surface such as a conductive material including a conductive metal solution. In embodiments "printing" or "painted" can comprise any method of applying a solution to a material upon which a matrix is desired. It is also assumed that a competent practitioner knows how to properly apply and cure the solutions without any assistance, other than perhaps instructions that should be included with the selected binder that is used to make the mixtures that will be used in the printing process.

A preferred material to use in combination with silver to create the voltaic cells or reservoirs of disclosed embodiments is zinc. Zinc has been well-described for its uses in prevention of infection in such topical antibacterial agents as Bacitracin zinc, a zinc salt of Bacitracin. Zinc is a divalent cation with antibacterial properties of its own in addition to possessing the added benefit of being a cofactor to proteins of the metalloproteinase family of enzymes important to the phagocytic debridement and remodeling phases of wound healing. As a cofactor zinc promotes and accelerates the functional activity of these enzymes, resulting in better more efficient wound healing.

Turning to the figures, in FIG. 1, the dissimilar electrodes first electrode 6 and second electrode 10 are applied onto a desired primary surface 2 of an article 4. In one embodiment primary surface is a surface of a LLMC or LLEF system that comes into direct contact with an area to be treated such as skin surface or a wound. In alternate embodiments primary surface 2 is one which is desired to be antimicrobial, such as a medical instrument, implant, surgical gown, gloves, socks, table, door knob, or other surface that will contact an electrolytic solution including sweat, so that at least part of the pattern of voltaic cells will spontaneously react and kill bacteria or other microbes.

In various embodiments the difference of the standard potentials of the electrodes or dots or reservoirs can be in a range from 0.05 V to approximately 5.0 V. For example, the standard potential can be 0.05 V, 0.06 V, 0.07 V, 0.08 V, 0.09 V, 0.1 V, 0.2 V, or 0.3 V, 0.4 V, 0.5 V, 0.6 V, 0.7 V, 0.8 V, 0.9 V, 1.0 V, 1.1 V, 1.2 V, 1.3 V, 1.4 V, 1.5 V, 1.6 V, 1.7 V, 1.8 V, 1.9 V, 2.0 V, 2.1 V, 2.2 V, 2.3 V, 2.4 V, 2.5 V, 2.6 V, 2.7 V, 2.8 V, 2.9 V, 3.0 V, 3.1 V, 3.2 V, 3.3 V, 3.4 V, 3.5 V, 3.6 V, 3.7 V, 3.8 V, 3.9 V, 4.0 V, 4.1 V, 4.2 V, 4.3 V, 4.4 V, 4.5 V, 4.6 V, 4.7 V, 4.8 V, 4.9 V, 5.0 V, 5.1 V, 5.2 V, 5.3 V, 5.4 V, 5.5 V, 5.6 V, 5.7 V, 5.8 V, 5.9 V, 6.0 V, or the like.

In a particular embodiment, the difference of the standard potentials of the electrodes or dots or reservoirs can be at least 0.05 V, at least 0.06 V, at least 0.07 V, at least 0.08 V, at least 0.09 V, at least 0.1 V, at least 0.2 V, at least 0.3 V, at least 0.4 V, at least 0.5 V, at least 0.6 V, at least 0.7 V, at least 0.8 V, at least 0.9 V, at least 1.0 V, at least 1.1 V, at least 1.2 V, at least 1.3 V, at least 1.4 V, at least 1.5 V, at least 1.6 V, at least 1.7 V, at least 1.8 V, at least 1.9 V, at least 2.0 V, at least 2.1 V, at least 2.2 V, at least 2.3 V, at least 2.4 V, at least 2.5 V, at least 2.6 V, at least 2.7 V, at least 2.8 V, at least 2.9 V, at least 3.0 V, at least 3.1 V, at least 3.2 V, at least 3.3 V, at least 3.4 V, at least 3.5 V, at least 3.6 V, at least 3.7 V, at least 3.8 V, at least 3.9 V, at least 4.0 V, at least 4.1 V, at least 4.2 V, at least 4.3 V, at least 4.4 V, at least 4.5 V, at least 4.6 V, at least 4.7 V, at least 4.8 V, at least 4.9 V, at least 5.0 V, at least 5.1 V, at least 5.2 V, at least 5.3 V, at least 5.4 V, at least 5.5 V, at least 5.6 V, at least 5.7 V, at least 5.8 V, at least 5.9 V, at least 6.0 V, or the like.

In a particular embodiment, the difference of the standard potentials of the electrodes or dots or reservoirs can be not more than 0.05 V, or not more than 0.06 V, not more than 0.07 V, not more than 0.08 V, not more than 0.09 V, not more than 0.1 V, not more than 0.2 V, not more than 0.3 V, not more than 0.4 V, not more than 0.5 V, not more than 0.6 V, not more than 0.7 V, not more than 0.8 V, not more than 0.9 V, not more than 1.0 V, not more than 1.1 V, not more than 1.2 V, not more than 1.3 V, not more than 1.4 V, not more than 1.5 V, not more than 1.6 V, not more than 1.7 V, not more than 1.8 V, not more than 1.9 V, not more than 2.0 V, not more than 2.1 V, not more than 2.2 V, not more than 2.3 V, not more than 2.4 V, not more than 2.5 V, not more than 2.6 V, not more than 2.7 V, not more than 2.8 V, not more than 2.9 V, not more than 3.0 V, not more than 3.1 V, not more than 3.2 V, not more than 3.3 V, not more than 3.4 V, not more than 3.5 V, not more than 3.6 V, not more than 3.7 V, not more than 3.8 V, not more than 3.9 V, not more than 4.0 V, not more than 4.1 V, not more than 4.2 V, not more than 4.3 V, not more than 4.4 V, not more than 4.5 V, not more than 4.6 V, not more than 4.7 V, not more than 4.8 V, not more than 4.9 V, not more than 5.0 V, not more than 5.1 V, not more than 5.2 V, not more than 5.3 V, not more than 5.4 V, not more than 5.5 V, not more than 5.6 V, not more than 5.7 V, not more than 5.8 V, not more than 5.9 V, not more than 6.0 V, or the like.

In embodiments, LLMC systems can produce a low level micro-current of between for example about 1 and about 200 micro-amperes, between about 10 and about 190 micro-amperes, between about 20 and about 180 micro-amperes, between about 30 and about 170 micro-amperes, between about 40 and about 160 micro-amperes, between about 50 and about 150 micro-amperes, between about 60 and about 140 micro-amperes, between about 70 and about 130 micro-amperes, between about 80 and about 120 micro-amperes, between about 90 and about 100 micro-amperes, or the like.

In embodiments, LLMC systems can produce a low level micro-current of between for example about 1 and about 400 micro-amperes, between about 20 and about 380 micro-amperes, between about 400 and about 360 micro-amperes, between about 60 and about 340 micro-amperes, between about 80 and about 320 micro-amperes, between about 100 and about 3000 micro-amperes, between about 120 and about 280 micro-amperes, between about 140 and about 260 micro-amperes, between about 160 and about 240 micro-amperes, between about 180 and about 220 micro-amperes, or the like.

In embodiments, LLMC systems of the invention can produce a low level micro-current about 10 micro-amperes, about 20 micro-amperes, about 30 micro-amperes, about 40 micro-amperes, about 50 micro-amperes, about 60 micro-amperes, about 70 micro-amperes, about 80 micro-amperes, about 90 micro-amperes, about 100 micro-amperes, about 110 micro-amperes, about 120 micro-amperes, about 130 micro-amperes, about 140 micro-amperes, about 150 micro-amperes, about 160 micro-amperes, about 170 micro-amperes, about 180 micro-amperes, about 190 micro-amperes, about 200 micro-amperes, about 210 micro-amperes, about 220 micro-amperes, about 240 micro-amperes, about 260 micro-amperes, about 280 micro-amperes, about 300 micro-amperes, about 320 micro-amperes, about 340 micro-amperes, about 360 micro-amperes, about 380 micro-amperes, about 400 micro-amperes, or the like.

In embodiments, LLMC systems can produce a low level micro-current of not more than 10 micro-amperes, or not more than 20 micro-amperes, not more than 30 micro-amperes, not more than 40 micro-amperes, not more than 50 micro-amperes, not more than 60 micro-amperes, not more than 70 micro-amperes, not more than 80 micro-amperes, not more than 90 micro-amperes, not more than 100 micro-amperes, not more than 110 micro-amperes, not more than 120 micro-amperes, not more than 130 micro-amperes, not more than 140 micro-amperes, not more than 150 micro-amperes, not more than 160 micro-amperes, not more than 170 micro-amperes, not more than 180 micro-amperes, not more than 190 micro-amperes, not more than 200 micro-amperes, not more than 210 micro-amperes, not more than 220 micro-amperes, not more than 230 micro-amperes, not more than 240 micro-amperes, not more than 250 micro-amperes, not more than 260 micro-amperes, not more than 270 micro-amperes, not more than 280 micro-amperes, not more than 290 micro-amperes, not more than 300 micro-amperes, not more than 310 micro-amperes, not more than 320 micro-amperes, not more than 340 micro-amperes, not more than 360 micro-amperes, not more than 380 micro-amperes, not more than 400 micro-amperes, not more than 420 micro-amperes, not more than 440 micro-amperes, not more than 460 micro-amperes, not more than 480 micro-amperes, or the like.

In embodiments, LLMC systems of the invention can produce a low level micro-current of not less than 10 micro-amperes, not less than 20 micro-amperes, not less than 30 micro-amperes, not less than 40 micro-amperes, not less than 50 micro-amperes, not less than 60 micro-amperes, not less than 70 micro-amperes, not less than 80 micro-amperes, not less than 90 micro-amperes, not less than 100 micro-amperes, not less than 110 micro-amperes, not less than 120 micro-amperes, not less than 130 micro-amperes, not less than 140 micro-amperes, not less than 150 micro-amperes, not less than 160 micro-amperes, not less than 170 micro-amperes, not less than 180 micro-amperes, not less than 190 micro-amperes, not less than 200 micro-amperes, not less than 210 micro-amperes, not less than 220 micro-amperes, not less than 230 micro-amperes, not less than 240 micro-amperes, not less than 250 micro-amperes, not less than 260 micro-amperes, not less than 270 micro-amperes, not less than 280 micro-amperes, not less than 290 micro-amperes, not less than 300 micro-amperes, not less than 310 micro-amperes, not less than 320 micro-amperes, not less than 330 micro-amperes, not less than 340 micro-amperes, not less than 350 micro-amperes, not less than 360 micro-amperes, not less than 370 micro-amperes, not less than 380 micro-amperes, not less than 390 micro-amperes, not less than 400 micro-amperes, or the like.

The applied electrodes or reservoirs or dots can adhere or bond to the primary surface 2 because a biocompatible binder is mixed, in embodiments into separate mixtures, with each of the dissimilar metals that create the pattern of voltaic cells, in embodiments. Most inks are simply a carrier, and a binder mixed with pigment. Similarly, conductive metal solutions can be a binder mixed with a conductive element. The resulting conductive metal solutions can be used with an application method such as screen printing to apply the electrodes to the primary surface in predetermined patterns. Once the conductive metal solutions dry and/or cure, the patterns of spaced electrodes can substantially maintain their relative position, even on a flexible material such as that used for a LLMC or LLEF system. To make a limited number of the systems of an embodiment disclosed herein, the conductive metal solutions can be hand applied onto a common adhesive bandage so that there is an array of alternating electrodes that are spaced about a millimeter apart on the primary surface of the bandage. The solution should be allowed to dry before being applied to a surface so that the conductive materials do not mix, which would destroy the array and cause direct reactions that will release the elements, but fail to simulate the current of injury. However, the wound management system would still exhibit an antimicrobial effect even if the materials were mixed. Furthermore, though silver alone will demonstrate antimicrobial effects, embodiments of the invention show antimicrobial activity greater than that of silver alone.

In certain embodiments that utilize a poly-cellulose binder, the binder itself can have an beneficial effect such as reducing the local concentration of matrix metallo-proteases through an iontophoretic process that drives the cellulose into the surrounding tissue. This process can be used to electronically drive other components such as drugs into the surrounding tissue.

The binder can include any biocompatible liquid material that can be mixed with a conductive element (preferably metallic crystals of silver or zinc) to create a conductive solution which can be applied as a thin coating to a surface. One suitable binder is a solvent reducible polymer, such as the polyacrylic non-toxic silk-screen ink manufactured by COLORCON® Inc., a division of Berwind Pharmaceutical Services, Inc. (see COLORCON® NO-TOX® product line, part number NT28). In an embodiment the binder is mixed with high purity (at least 99.999%) metallic silver crystals to make the silver conductive solution. The silver crystals, which can be made by grinding silver into a powder, are preferably smaller than 100 microns in size or about as fine as flour. In an embodiment, the size of the crystals is about 325 mesh, which is typically about 40 microns in size or a little smaller. The binder is separately mixed with high purity (at least 99.99%, in an embodiment) metallic zinc powder which has also preferably been sifted through standard 325 mesh screen, to make the zinc conductive solution. For better quality control and more consistent results, most of the crystals used should be larger than 325 mesh and smaller than 200 mesh. For example the crystals used should be between 200 mesh and 325 mesh, or between 210 mesh and 310 mesh, between 220 mesh and 300 mesh, between 230 mesh and 290 mesh, between 240 mesh and 280 mesh, between 250 mesh and 270 mesh, between 255 mesh and 265 mesh, or the like.

Other powders of metal can be used to make other conductive metal solutions in the same way as described in other embodiments.

The size of the metal crystals, the availability of the surface to the conductive fluid and the ratio of metal to binder can affect the release rate of the metal from the mixture. When COLORCON® polyacrylic ink is used as the binder, about 10 to 40 percent of the mixture should be metal for a longer term bandage (for example, one that stays on for about 10 days). For example, for a longer term LLMC or LLEF system the percent of the mixture that should be metal can be 8 percent, or 10 percent, 12 percent, 14 percent, 16 percent, 18 percent, 20 percent, 22 percent, 24 percent, 26 percent, 28 percent, 30 percent, 32 percent, 34 percent, 36 percent, 38 percent, 40 percent, 42 percent, 44 percent, 46 percent, 48 percent, 50 percent, or the like.

If the same binder is used, but the percentage of the mixture that is metal is increased to 60 percent or higher, then the release rate will be much faster and a typical system will only be effective for a few days. For example, for a shorter term bandage, the percent of the mixture that should be metal can be 40 percent, or 42 percent, 44 percent, 46 percent, 48 percent, 50 percent, 52 percent, 54 percent, 56 percent, 58 percent, 60 percent, 62 percent, 64 percent, 66 percent, 68 percent, 70 percent, 72 percent, 74 percent, 76 percent, 78 percent, 80 percent, 82 percent, 84 percent, 86 percent, 88 percent, 90 percent, or the like.

It should be noted that polyacrylic ink can crack if applied as a very thin coat, which exposes more metal crystals which will spontaneously react. For LLMC or LLEF systems comprising an article of clothing it may be desired to decrease the percentage of metal down to 5 percent or less, or to use a binder that causes the crystals to be more deeply embedded, so that the primary surface will be antimicrobial for a very long period of time and will not wear prematurely. Other binders can dissolve or otherwise break down faster or slower than a polyacrylic ink, so adjustments can be made to achieve the desired rate of spontaneous reactions from the voltaic cells.

To maximize the number of voltaic cells, in various embodiments, a pattern of alternating silver masses or electrodes or reservoirs and zinc masses or electrodes or reservoirs can create an array of electrical currents across the primary surface. A basic pattern, shown in FIG. 1, has each mass of silver equally spaced from four masses of zinc, and has each mass of zinc equally spaced from four masses of silver, according to an embodiment. The first electrode 6 is separated from the second electrode 10 by a spacing 8. The designs of first electrode 6 and second electrode 10 are simply round dots, and in an embodiment, are repeated. Numerous repetitions 12 of the designs result in a pattern. For a wound management system or dressing, each silver design preferably has about twice as much mass as each zinc design, in an embodiment. For the pattern in FIG. 1, the silver designs are most preferably about a millimeter from each of the closest four zinc designs, and vice-versa. The resulting pattern of dissimilar metal masses defines an array of voltaic cells when introduced to an electrolytic solution. Further disclosure relating to methods of producing microarrays can be found in U.S. Pat. No. 7,813,806 entitled CURRENT PRODUCING SURFACE FOR TREATING BIOLOGIC TISSUE issued Oct. 12, 2010, which is incorporated by reference in its entirety.

A dot pattern of masses like the alternating round dots of FIG. 1 can be preferred when applying conductive material onto a flexible material, such as those used for a wound dressing, because the dots won't significantly affect the flexibility of the material. The pattern of FIG. 1 is well suited for general use. To maximize the density of electrical current over a primary surface the pattern of FIG. 2 can be used. The first electrode 6 in FIG. 2 is a large hexagonally shaped dot, and the second electrode 10 is a pair of smaller hexagonally shaped dots that are spaced from each other. The spacing 8 that is between the first electrode 6 and the second electrode 10 maintains a relatively consistent distance between adjacent sides of the designs. Numerous repetitions 12 of the designs result in a pattern 14 that can be described as at least one of the first design being surrounded by six hexagonally shaped dots of the second design. The pattern of FIG. 2 is well suited for abrasions and burns, as well as for insect bites, including those that can transfer bacteria or microbes or other organisms from the insect. There are of course other patterns that could be printed to achieve similar results.

FIGS. 3 and 4 show how the pattern of FIG. 2 can be used to make an adhesive bandage. The pattern shown in detail in FIG. 2 is applied to the primary surface 2 of a wound dressing material. The back 20 of the printed dressing material is fixed to an absorbent wound dressing layer 22 such as cotton. The absorbent dressing layer is adhesively fixed to an elastic adhesive layer 16 such that there is at least one overlapping piece or anchor 18 of the elastic adhesive layer that can be used to secure the wound management system over a wound.

FIG. 5 shows an additional feature, which can be added between designs, that will start the flow of current in a poor electrolytic solution. A fine line 24 is printed using one of the conductive metal solutions along a current path of each voltaic cell. The fine line will initially have a direct reaction but will be depleted until the distance between the electrodes increases to where maximum voltage is realized. The initial current produced is intended to help control edema so that the LLMC system will be effective. If the electrolytic solution is highly conductive when the system is initially applied the fine line can be quickly depleted and the wound dressing will function as though the fine line had never existed.

Figure 6:
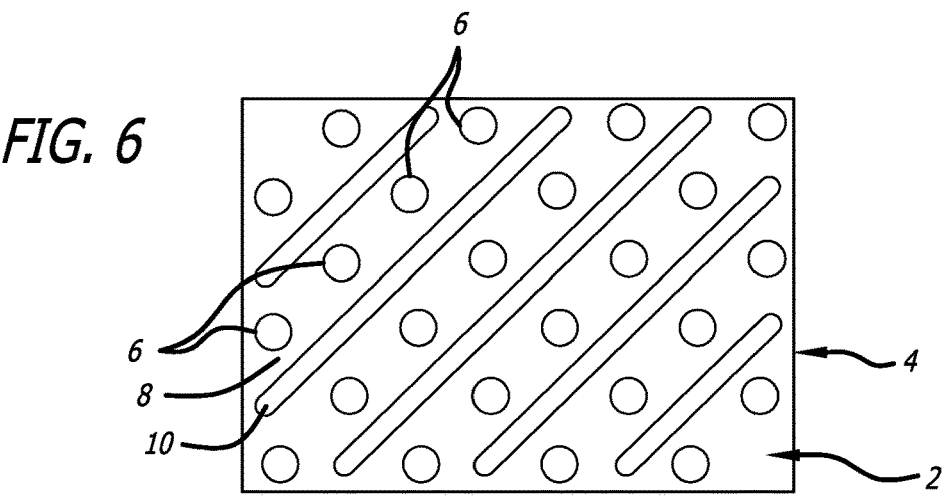
FIG. 6 is a detailed plan view of another alternate embodiment having a line pattern and dot pattern.
Figure 7:
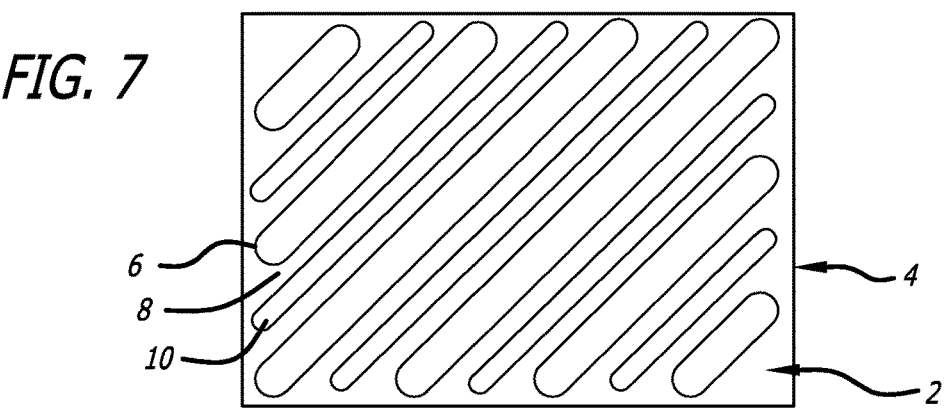
FIG. 7 is a detailed plan view of yet another alternate embodiment having two line patterns.
Figure 8A:
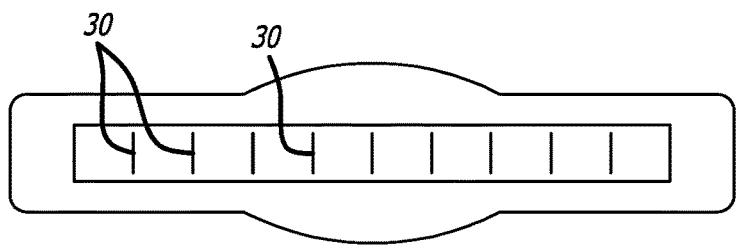
FIG. 8 depicts alternate embodiments showing the location of discontinuous regions as well as anchor regions of the wound management system.
Figure 8B:
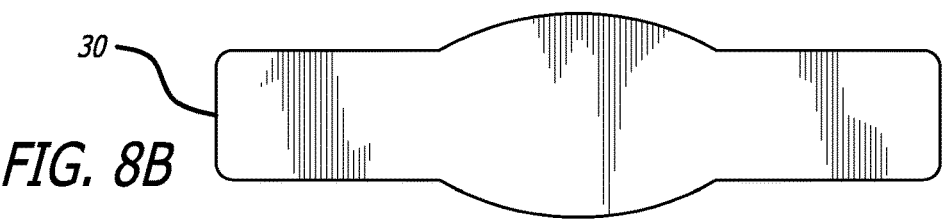
Figure 8C:
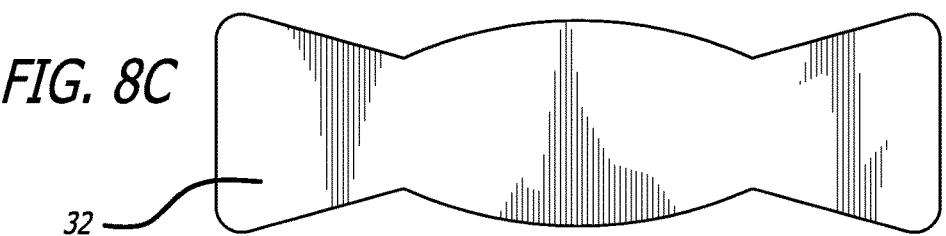
Figure 8D:
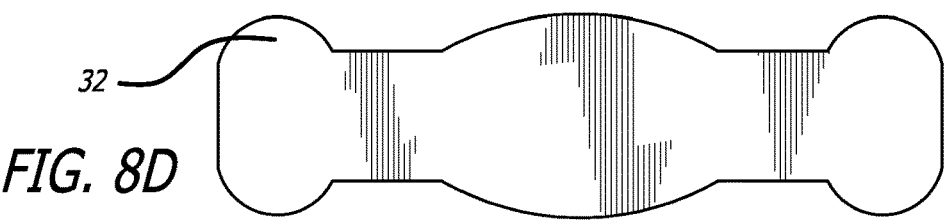
Figure 8E:
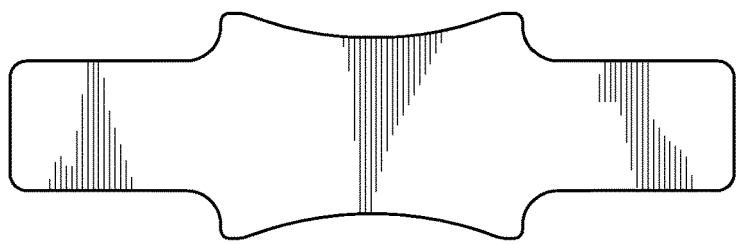

FIGS. 6 and 7 show alternative patterns that use at least one line design. The first electrode 6 of FIG. 6 is a round dot similar to the first design used in FIG. 1. The second electrode 10 of FIG. 6 is a line. When the designs are repeated, they define a pattern of parallel lines that are separated by numerous spaced dots. FIG. 7 uses only line designs. The pattern of FIG. 7 is well suited for cuts, especially when the lines are perpendicular to a cut. The first electrode 6 can be thicker or wider than the second electrode 10 if the oxidation-reduction reaction requires more metal from the first conductive element (mixed into the first design's conductive metal solution) than the second conductive element (mixed into the second design's conductive metal solution). The lines can be dashed. Another pattern can be silver grid lines that have zinc masses in the center of each of the cells of the grid. The pattern can be letters printed from alternating conductive materials so that a message can be printed onto the primary surface-perhaps a brand name or identifying information such as patient blood type.

Because the spontaneous oxidation-reduction reaction of silver and zinc uses a ratio of approximately two silver to one zinc, the silver design can contain about twice as much mass as the zinc design in an embodiment. At a spacing of about 1 mm between the closest dissimilar metals (closest edge to closest edge) each voltaic cell that is in wound fluid can create approximately 1 volt of potential that will penetrate substantially through the dermis and epidermis. Closer spacing of the dots can decrease the resistance, providing less potential, and the current will not penetrate as deeply. If the spacing falls below about one tenth of a millimeter a benefit of the spontaneous reaction is that which is also present with a direct reaction; silver is electrically driven into the wound, but the current of injury may not be substantially simulated. Therefore, spacing between the closest conductive materials can be 0.1 mm, or 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, or the like.

In certain embodiments the spacing between the closest conductive materials can be not more than 0.1 mm, or not more than 0.2 mm, not more than 0.3 mm, not more than 0.4 mm, not more than 0.5 mm, not more than 0.6 mm, not more than 0.7 mm, not more than 0.8 mm, not more than 0.9 mm, not more than 1 mm, not more than 1.1 mm, not more than 1.2 mm, not more than 1.3 mm, not more than 1.4 mm, not more than 1.5 mm, not more than 1.6 mm, not more than 1.7 mm, not more than 1.8 mm, not more than 1.9 mm, not more than 2 mm, not more than 2.1 mm, not more than 2.2 mm, not more than 2.3 mm, not more than 2.4 mm, not more than 2.5 mm, not more than 2.6 mm, not more than 2.7 mm, not more than 2.8 mm, not more than 2.9 mm, not more than 3 mm, not more than 3.1 mm, not more than 3.2 mm, not more than 3.3 mm, not more than 3.4 mm, not more than 3.5 mm, not more than 3.6 mm, not more than 3.7 mm, not more than 3.8 mm, not more than 3.9 mm, not more than 4 mm, not more than 4.1 mm, not more than 4.2 mm, not more than 4.3 mm, not more than 4.4 mm, not more than 4.5 mm, not more than 4.6 mm, not more than 4.7 mm, not more than 4.8 mm, not more than 4.9 mm, not more than 5 mm, not more than 5.1 mm, not more than 5.2 mm, not more than 5.3 mm, not more than 5.4 mm, not more than 5.5 mm, not more than 5.6 mm, not more than 5.7 mm, not more than 5.8 mm, not more than 5.9 mm, not more than 6 mm, or the like.

In certain embodiments spacing between the closest conductive materials can be not less than 0.1 mm, or not less than 0.2 mm, not less than 0.3 mm, not less than 0.4 mm, not less than 0.5 mm, not less than 0.6 mm, not less than 0.7 mm, not less than 0.8 mm, not less than 0.9 mm, not less than 1 mm, not less than 1.1 mm, not less than 1.2 mm, not less than 1.3 mm, not less than 1.4 mm, not less than 1.5 mm, not less than 1.6 mm, not less than 1.7 mm, not less than 1.8 mm, not less than 1.9 mm, not less than 2 mm, not less than 2.1 mm, not less than 2.2 mm, not less than 2.3 mm, not less than 2.4 mm, not less than 2.5 mm, not less than 2.6 mm, not less than 2.7 mm, not less than 2.8 mm, not less than 2.9 mm, not less than 3 mm, not less than 3.1 mm, not less than 3.2 mm, not less than 3.3 mm, not less than 3.4 mm, not less than 3.5 mm, not less than 3.6 mm, not less than 3.7 mm, not less than 3.8 mm, not less than 3.9 mm, not less than 4 mm, not less than 4.1 mm, not less than 4.2 mm, not less than 4.3 mm, not less than 4.4 mm, not less than 4.5 mm, not less than 4.6 mm, not less than 4.7 mm, not less than 4.8 mm, not less than 4.9 mm, not less than 5 mm, not less than 5.1 mm, not less than 5.2 mm, not less than 5.3 mm, not less than 5.4 mm, not less than 5.5 mm, not less than 5.6 mm, not less than 5.7 mm, not less than 5.8 mm, not less than 5.9 mm, not less than 6 mm, or the like.

Disclosures of the present specification include LLMC or LLEF systems comprising a primary surface of a pliable material wherein the pliable material is adapted to be applied to an area of tissue; a first electrode design formed from a first conductive liquid that includes a mixture of a polymer and a first element, the first conductive liquid being applied into a position of contact with the primary surface, the first element including a metal species, and the first electrode design including at least one dot or reservoir, wherein selective ones of the at least one dot or reservoir have approximately a 1.5 mm+/−1 mm mean diameter; a second electrode design formed from a second conductive liquid that includes a mixture of a polymer and a second element, the second element including a different metal species than the first element, the second conductive liquid being printed into a position of contact with the primary surface, and the second electrode design including at least one other dot or reservoir, wherein selective ones of the at least one other dot or reservoir have approximately a 2.5 mm+/−2 mm mean diameter; a spacing on the primary surface that is between the first electrode design and the second electrode design such that the first electrode design does not physically contact the second electrode design, wherein the spacing is approximately 1.5 mm+/−1 mm, and at least one repetition of the first electrode design and the second electrode design, the at least one repetition of the first electrode design being substantially adjacent the second electrode design, wherein the at least one repetition of the first electrode design and the second electrode design, in conjunction with the spacing between the first electrode design and the second electrode design, defines at least one pattern of at least one voltaic cell for spontaneously generating at least one electrical current when introduced to an electrolytic solution. Therefore, electrodes, dots or reservoirs can have a mean diameter of 0.2 mm, or 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, 5.0 mm, or the like.

In further embodiments, electrodes, dots or reservoirs can have a mean diameter of not less than 0.2 mm, or not less than 0.3 mm, not less than 0.4 mm, not less than 0.5 mm, not less than 0.6 mm, not less than 0.7 mm, not less than 0.8 mm, not less than 0.9 mm, not less than 1.0 mm, not less than 1.1 mm, not less than 1.2 mm, not less than 1.3 mm, not less than 1.4 mm, not less than 1.5 mm, not less than 1.6 mm, not less than 1.7 mm, not less than 1.8 mm, not less than 1.9 mm, not less than 2.0 mm, not less than 2.1 mm, not less than 2.2 mm, not less than 2.3 mm, not less than 2.4 mm, not less than 2.5 mm, not less than 2.6 mm, not less than 2.7 mm, not less than 2.8 mm, not less than 2.9 mm, not less than 3.0 mm, not less than 3.1 mm, not less than 3.2 mm, not less than 3.3 mm, not less than 3.4 mm, not less than 3.5 mm, not less than 3.6 mm, not less than 3.7 mm, not less than 3.8 mm, not less than 3.9 mm, not less than 4.0 mm, not less than 4.1 mm, not less than 4.2 mm, not less than 4.3 mm, not less than 4.4 mm, not less than 4.5 mm, not less than 4.6 mm, not less than 4.7 mm, not less than 4.8 mm, not less than 4.9 mm, not less than 5.0 mm, or the like.

In further embodiments, electrodes, dots or reservoirs can have a mean diameter of not more than 0.2 mm, or not more than 0.3 mm, not more than 0.4 mm, not more than 0.5 mm, not more than 0.6 mm, not more than 0.7 mm, not more than 0.8 mm, not more than 0.9 mm, not more than 1.0 mm, not more than 1.1 mm, not more than 1.2 mm, not more than 1.3 mm, not more than 1.4 mm, not more than 1.5 mm, not more than 1.6 mm, not more than 1.7 mm, not more than 1.8 mm, not more than 1.9 mm, not more than 2.0 mm, not more than 2.1 mm, not more than 2.2 mm, not more than 2.3 mm, not more than 2.4 mm, not more than 2.5 mm, not more than 2.6 mm, not more than 2.7 mm, not more than 2.8 mm, not more than 2.9 mm, not more than 3.0 mm, not more than 3.1 mm, not more than 3.2 mm, not more than 3.3 mm, not more than 3.4 mm, not more than 3.5 mm, not more than 3.6 mm, not more than 3.7 mm, not more than 3.8 mm, not more than 3.9 mm, not more than 4.0 mm, not more than 4.1 mm, not more than 4.2 mm, not more than 4.3 mm, not more than 4.4 mm, not more than 4.5 mm, not more than 4.6 mm, not more than 4.7 mm, not more than 4.8 mm, not more than 4.9 mm, not more than 5.0 mm, or the like.

The material concentrations or quantities within and/or the relative sizes (e.g., dimensions or surface area) of the first and second reservoirs can be selected deliberately to achieve various characteristics of the systems' behavior. For example, the quantities of material within a first and second reservoir can be selected to provide an apparatus having an operational behavior that depletes at approximately a desired rate and/or that "dies" after an approximate period of time after activation. In an embodiment the one or more first reservoirs and the one or more second reservoirs are configured to sustain one or more currents for an approximate pre-determined period of time, after activation. It is to be understood that the amount of time that currents are sustained can depend on external conditions and factors (e.g., the quantity and type of activation material), and currents can occur intermittently depending on the presence or absence of activation material. Further disclosure relating to producing reservoirs that are configured to sustain one or more currents for an approximate pre-determined period of time can be found in U.S. Pat. No. 7,904,147 entitled SUBSTANTIALLY PLANAR ARTICLE AND METHODS OF MANUFACTURE issued Mar. 8, 2011, which is incorporated by reference herein in its entirety.

In various embodiments the difference of the standard potentials of the first and second reservoirs can be in a range from 0.05 V to approximately 5.0 V. For example, the standard potential can be 0.05 V, or 0.06 V, 0.07 V, 0.08 V, 0.09 V, 0.1 V, 0.2 V, 0.3 V, 0.4 V, 0.5 V, 0.6 V, 0.7 V, 0.8 V, 0.9 V, 1.0 V, 1.1 V, 1.2 V, 1.3 V, 1.4 V, 1.5 V, 1.6 V, 1.7 V, 1.8 V, 1.9 V, 2.0 V, 2.1 V, 2.2 V, 2.3 V, 2.4 V, 2.5 V, 2.6 V, 2.7 V, 2.8 V, 2.9 V, 3.0 V, 3.1 V, 3.2 V, 3.3 V, 3.4 V, 3.5 V, 3.6 V, 3.7 V, 3.8 V, 3.9 V, 4.0 V, 4.1 V, 4.2 V, 4.3 V, 4.4 V, 4.5 V, 4.6 V, 4.7 V, 4.8 V, 4.9 V, 5.0 V, or the like.

In a particular embodiment the difference of the standard potentials of the first and second reservoirs can be at least 0.05 V, or at least 0.06 V, at least 0.07 V, at least 0.08 V, at least 0.09 V, at least 0.1 V, at least 0.2 V, at least 0.3 V, at least 0.4 V, at least 0.5 V, at least 0.6 V, at least 0.7 V, at least 0.8 V, at least 0.9 V, at least 1.0 V, at least 1.1 V, at least 1.2 V, at least 1.3 V, at least 1.4 V, at least 1.5 V, at least 1.6 V, at least 1.7 V, at least 1.8 V, at least 1.9 V, at least 2.0 V, at least 2.1 V, at least 2.2 V, at least 2.3 V, at least 2.4 V, at least 2.5 V, at least 2.6 V, at least 2.7 V, at least 2.8 V, at least 2.9 V, at least 3.0 V, at least 3.1 V, at least 3.2 V, at least 3.3 V, at least 3.4 V, at least 3.5 V, at least 3.6 V, at least 3.7 V, at least 3.8 V, at least 3.9 V, at least 4.0 V, at least 4.1 V, at least 4.2 V, at least 4.3 V, at least 4.4 V, at least 4.5 V, at least 4.6 V, at least 4.7 V, at least 4.8 V, at least 4.9 V, at least 5.0 V, or the like.

In a particular embodiment, the difference of the standard potentials of the first and second reservoirs can be not more than 0.05 V, or not more than 0.06 V, not more than 0.07 V, not more than 0.08 V, not more than 0.09 V, not more than 0.1 V, not more than 0.2 V, not more than 0.3 V, not more than 0.4 V, not more than 0.5 V, not more than 0.6 V, not more than 0.7 V, not more than 0.8 V, not more than 0.9 V, not more than 1.0 V, not more than 1.1 V, not more than 1.2 V, not more than 1.3 V, not more than 1.4 V, not more than 1.5 V, not more than 1.6 V, not more than 1.7 V, not more than 1.8 V, not more than 1.9 V, not more than 2.0 V, not more than 2.1 V, not more than 2.2 V, not more than 2.3 V, not more than 2.4 V, not more than 2.5 V, not more than 2.6 V, not more than 2.7 V, not more than 2.8 V, not more than 2.9 V, not more than 3.0 V, not more than 3.1 V, not more than 3.2 V, not more than 3.3 V, not more than 3.4 V, not more than 3.5 V, not more than 3.6 V, not more than 3.7 V, not more than 3.8 V, not more than 3.9 V, not more than 4.0 V, not more than 4.1 V, not more than 4.2 V, not more than 4.3 V, not more than 4.4 V, not more than 4.5 V, not more than 4.6 V, not more than 4.7 V, not more than 4.8 V, not more than 4.9 V, not more than 5.0 V, or the like. In embodiments that include very small reservoirs (e.g., on the nanometer scale), the difference of the standard potentials can be substantially less or more. The electrons that pass between the first reservoir and the second reservoir can be generated as a result of the difference of the standard potentials. Further disclosure relating to standard potentials can be found in U.S. Pat. No. 8,224,439 entitled BATTERIES AND METHODS OF MANUFACTURE AND USE issued Jul. 17, 2012, which is incorporated be reference herein in its entirety.

The voltage present at the site of treatment is typically in the range of millivolts but disclosed embodiments can introduce a much higher voltage, for example near 1 volt when using the 1 mm spacing of dissimilar metals already described. The higher voltage is believed to drive the current deeper into the treatment area so that dermis and epidermis benefit from the simulated current of injury. In this way the current not only can drive silver and zinc into the treatment, but the current can also provide a stimulatory current so that the entire surface area can heal simultaneously. In embodiments the current can, for example, kill microbes.

Embodiments disclosed herein relating to treatment of diseases or conditions or symptoms can also comprise selecting a patient or tissue in need of, or that could benefit by, treatment of that disease, condition, or symptom.

While various embodiments have been shown and described, it will be realized that alterations and modifications can be made thereto without departing from the scope of the following claims. For example it can be desirable to use methods other than a common screen printing machine to apply the electrodes onto surfaces on medical instruments, garments, implants and the like so that they are antimicrobial. It is expected that other methods of applying the conductive material can be substituted as appropriate. Also, there are numerous shapes, sizes and patterns of voltaic cells that have not been described but it is expected that this disclosure will enable those skilled in the art to incorporate their own designs which will then be applied to a surface to create voltaic cells which will become active when brought into contact with an electrolytic solution.

Certain embodiments include LLMC or LLEF systems comprising dressings or bandages designed to be used on irregular, non-planar, or "stretching" surfaces such as joints. Embodiments disclosed herein can be used with numerous joints of the body, including the jaw, the shoulder, the elbow, the wrist, the finger joints, the hip, the knee, the ankle, the toe joints, etc. Additional embodiments disclosed herein can be used in areas where tissue is prone to movement, for example the eyelid, the ear, the lips, the nose, genitalia, etc.

Various apparatus embodiments which can be referred to as "medical batteries" are described herein. Further disclosure relating to this technology can be found in U.S. Pat. No. 7,672,719 entitled BATTERIES AND METHODS OF MANUFACTURE AND USE issued Mar. 2, 2010, which is incorporated herein by reference in its entirety.

Certain embodiments disclosed herein include a method of manufacturing a substantially planar LLMC or LLEF system, the method comprising joining with a substrate multiple first reservoirs wherein selected ones of the multiple first reservoirs include a reducing agent, and wherein first reservoir surfaces of selected ones of the multiple first reservoirs are proximate to a first substrate surface; and joining with the substrate multiple second reservoirs wherein selected ones of the multiple second reservoirs include an oxidizing agent, and wherein second reservoir surfaces of selected ones of the multiple second reservoirs are proximate to the first substrate surface, wherein joining the multiple first reservoirs and joining the multiple second reservoirs comprises joining using tattooing. In embodiments the substrate can comprise gauzes comprising dots or electrodes.

Further embodiments can include a method of manufacturing a LLMC or LLEF system, the method comprising joining with a substrate multiple first reservoirs wherein selected ones of the multiple first reservoirs include a reducing agent, and wherein first reservoir surfaces of selected ones of the multiple first reservoirs are proximate to a first substrate surface; and joining with the substrate multiple second reservoirs wherein selected ones of the multiple second reservoirs include an oxidizing agent, and wherein second reservoir surfaces of selected ones of the multiple second reservoirs are proximate to the first substrate surface, wherein joining the multiple first reservoirs and joining the multiple second reservoirs comprises: combining the multiple first reservoirs, the multiple second reservoirs, and multiple parallel insulators to produce a pattern repeat arranged in a first direction across a plane, the pattern repeat including a sequence of a first one of the parallel insulators, one of the multiple first reservoirs, a second one of the parallel insulators, and one of the multiple second reservoirs; and weaving multiple transverse insulators through the first parallel insulator, the one first reservoir, the second parallel insulator, and the one second reservoir in a second direction across the plane to produce a woven apparatus.

Embodiments disclosed herein comprise combination therapies that include the use of biocompatible electrodes. Such combination therapies can include wound healing energy modalities, such as, for example, lasers, plasma, radio frequency, ultrasound, heat, light, and the like. For example in an embodiment the use of biocompatible electrodes is combined with NPWT, TOT, HBOT, MLCT, or the like.

In some embodiments reduced or negative pressure (e.g., below atmospheric pressure) can be used to assist with the healing of wounds. Certain embodiments can comprise multi-mode therapies wherein the negative pressure applied to the wound site is applied constantly, intermittently, or in levels that increase or decrease over time.

LLMC/LLEF Systems—Methods of Use

Embodiments disclosed herein include LLMC and LLEF systems that can produce an electrical stimulus and/or can electromotivate, electroconduct, electroinduct, electrotransport, and/or electrophorese one or more therapeutic materials in areas of target tissue (e.g., iontophoresis), and/or can cause one or more biologic or other materials in proximity to, on or within target tissue to be affected (e.g., attract, repel, kill, neutralize, or alter cellular growth/viability/mobility, etc.). Further disclosure relating to materials that can produce an electrical stimulus can be found in U.S. Pat. No. 7,662,176 entitled FOOTWEAR APPARATUS AND METHODS OF MANUFACTURE AND USE issued Feb. 16, 2010, which is incorporated herein by reference in its entirety.

Treatment of Wounds

The wound healing process includes several phases, including an inflammatory phase and a proliferative phase. The proliferative phase involves cell migration (such as by human keratinocytes) wherein cells migrate into the wound site and cell proliferation wherein the cells reproduce. This phase also involves angiogenesis and the growth of granulation tissue. During cell migration, many epithelial cells have the ability to detect electric fields and respond with directed migration. Their response typically requires $Ca^{2+}$ influx, the presence of specific growth factors such as Integrin and intracellular kinase activity. Most types of cells migrate directionally in a small electric field, a phenomenon called galvanotaxis or electrotaxis. Electric fields of strength equal to those detected at wound edges direct cell migration and can override some other well-accepted coexistent guidance cues such as contact inhibition. Aspects of the present specification disclose in part a method of treating an individual with a wound. Treating a wound can include covering the wound with a LLMC or LLEF system. Embodiments disclosed herein can promote wound healing by directing cell migration during the wound healing process.

In embodiments a wound can be an acute or chronic wound, a diabetic wound, such as one of the lower extremities, such as of the legs or feet, a post-radiation tissue injury, crush injuries or compartment syndrome and other acute traumatic ischemias, venous stasis or arterial-insufficiency ulcers, compromised grafts and flaps, infected wounds, pressure ulcers, necrotizing soft-tissue infections, burns, cancer-related wounds, osteomyelitis, surgical wounds, traumatic wounds, insect bites, and the like. In an embodiment a wound can be a non-penetrating wound, such as the result of blunt trauma or friction with other surfaces. Typically this type of wound does not break through the skin and may include an abrasion (scraping of the outer skin layer), a laceration (a tear-like wound), a contusion (swollen bruises due to accumulation of blood and dead cells under skin), or the like. In other embodiments a wound can be a penetrating wound. These result from trauma that breaks through the full thickness of skin and include stab wounds (trauma from sharp objects, such as knives), skin cuts, surgical wounds (intentional cuts in the skin to perform surgical procedures), shrapnel wounds (wounds resulting from exploding shells), or gunshot wounds (wounds resulting from firearms). In further embodiments a wound can be a thermal wound such as resulting from heat or cold, a chemical wound such as resulting from an acid or base, an electrical wound, or the like.

Chronic wounds often do not heal in normal stages, and the wounds can also fail to heal in a timely fashion. LLMC and LLEF systems disclosed herein can promote the healing of chronic wounds by increasing cell migration, cell proliferation, and/or cell signaling. Increased migration can be seen in various cell types, such as for example keratinocytes.

In embodiments, treating the wound can comprise applying a LLMC or LLEF system to the wound such that the system can stretch with movement of the wound, surrounding area, or both. In certain embodiments, the system can be stretched before application to the wound such that the wound management system "pulls" the wound edges together.

In embodiments, methods for treating or dressing a wound comprises the step of topically administering an additional material on the wound surface or upon the matrix of biocompatible microcells. These additional materials can comprise, for example, activation gels, rhPDGF (REGRANEX®), Vibronectin:IGF complexes, CELLSPRAY®, RECELL®, INTEGRA® dermal regeneration template, BIOMEND®, INFUSE®, ALLODERM®, CYMETRA®, SEPRAPACK®, SEPRAMESH®, SKINTEMP®, MEDFIL®, COSMODERM®, COSMOPLAST®, OP-1®, ISOLAGEN®, CARTICEL®, APLIGRAF®, DERMAGRAFT®, TRANSCYTE®, ORCEL®, EPICEL®, and the like. In embodiments the activation gel can be, for example, TEGADERM® 91110 by 3M, MEPILEX® Normal Gel 0.9% Sodium chloride, HISPAGEL®, LUBRIGEL®, or other compositions useful for maintaining a moist environment about the wound or useful for healing a wound via another mechanism.

Aspects of the present specification provide, in part, methods of reducing a symptom associated with a wound. In an aspect of this embodiment the symptom reduced is edema, hyperemia, erythema, bruising, tenderness, stiffness, swollenness, fever, a chill, a breathing problem, fluid retention, a blood clot, a loss of appetite, an increased heart rate, a formation of granulomas, fibrinous, pus, or non-viscous serous fluid, a formation of an ulcer, or pain.

Treating a wound can refer to reducing the size of, or preventing an increase in size of a wound. For example, treating can reduce the width of a wound by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%.

Treating a wound can refer to reducing the depth of, or preventing an increase in depth of a wound. For example, treating can reduce the depth of a wound by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%.

In some embodiments wounds are treated by using a NPWT system comprising a wound management system comprising a dressing comprising a multi-array matrix of biocompatible microcells, a fluid collection device, one or more conduits, filters, and a negative pressure source (e.g., a vacuum pump). In embodiments the wound dressing comprising a multi-array matrix of biocompatible microcells is placed inside the wound bed then covered with a flexible membrane, for example, a polymeric or elastomeric film. In certain embodiments the wound can be imaged such as in three dimensions (height, width, and depth) or two dimensions and the resulting information used to produce a wound management system comprising a dressing custom fit to the particular wound. In certain embodiments the wound management system comprises a pliable cover material that "seals" the wound bed to provide an air-tight seal. In embodiments the conduit providing negative pressure to the wound enters the wound under the wound management system or through a slit in the pliable cover material.

In some embodiments the system can be configured to provide a baseline negative pressure of approximately 10-12 mmHg below atmospheric pressure. For example, the baseline negative pressure can be 2 mmHg below atmospheric pressure, or 3 mmHg below atmospheric pressure, or 4 mmHg below atmospheric pressure, or 5 mmHg below atmospheric pressure, or 6 mmHg below atmospheric pressure, or 7 mmHg below atmospheric pressure, or 8 mmHg below atmospheric pressure, or 9 mmHg below atmospheric pressure, or 10 mmHg below atmospheric pressure, or 11 mmHg below atmospheric pressure, or 12 mmHg below atmospheric pressure, or 13 mmHg below atmospheric pressure, or 14 mmHg below atmospheric pressure, or 15 mmHg below atmospheric pressure, or 16 mmHg below atmospheric pressure, or 17 mmHg below atmospheric pressure, or 18 mmHg below atmospheric pressure, or 19 mmHg below atmospheric pressure, or 20 mmHg below atmospheric pressure or more, or the like.

In an embodiment, NPWT is administered for 90 minutes once a day for four days, followed by a three-day rest period. This cycle can be repeated for as long as the wound appears to be healing. For example in an embodiment NPWT can be applied for 20 minutes, or 30 minutes, or 40 minutes, or 50 minutes, or 60 minutes, or 70 minutes, or 80 minutes, or 90 minutes, or 100 minutes, or 110 minutes, or 120 minutes, or 130 minutes, or 140 minutes, or 150 minutes, or more, or the like. This can be repeated multiple times in a day, for example NPWT can be administered twice a day, or three times a day, or four times a day, or five times a day, or more, or the like. The therapy can be continued for 1 day, or 2 days, or 3 days, or 4 days, or 5 days, or 6 days, or 7 days, or 8 days, or 9 days, or 10 days, or 11 days, or 12 days, or 13 days, or 14 days, or 15 days, or 16 days, or 17 days, or 18 days, or 19 days, or 20 days or more, or the like.

In certain embodiments the NPWT can comprise rest periods between days of treatment. For example a rest period can be 1 day, or 2 days, or 3 days, or 4 days, or 5 days, or 6 days, or 7 days, or 8 days, or 9 days, or 10 days, or 11 days, or 12 days, or 13 days, or 14 days, or 15 days, or 16 days, or 17 days, or 18 days, or 19 days, or 20 days or more, or the like.

In some embodiments the system can be configured to apply cyclical reduced pressure to the wound in synchrony with the monitored heart activity of the patient received from one or more sensors. In some embodiments the control device can control the negative pressure source to apply a reduced pressure at a first amplitude during duration of systolic period, and to release the reduced pressure at the first amplitude to apply a reduced pressure at a second amplitude during duration of diastolic period. In some embodiments the control device can control the suction source to apply a reduced pressure at a first amplitude during duration of diastolic period, and to release the reduced pressure at the first amplitude to apply a reduced pressure at a second amplitude during duration of systolic period.

In some embodiments the system can be configured to apply cyclical reduced pressure to the wound in synchrony with the monitored blood flow through the wound received from one or more sensors.

In embodiments the negative pressure can be increased at a predetermined rate or cycle. For example the negative pressure applied to the wound can be increased by 10 mmHg, or 20 mmHg, or 40 mmHg, or 60 mmHg, or 80 mmHg, or 100 mmHg, or 120 mmHg, or 140 mmHg, or 160 mmHg, or 180 mmHg, or the like.

In embodiments the increase in negative pressure can be cycled at 10 cycles per minute, or 20 cycles per minute, or 30 cycles per minute, or 40 cycles per minute, or 50 cycles per minute, or 60 cycles per minute, or 80 cycles per minute, or 100 cycles per minute, or 120 cycles per minute or more, or the like.

In certain embodiments TOT can be used to assist with the healing of wounds. For example in some embodiments wounds are treated by using a TOT system comprising a wound management system comprising wound dressing comprising a multi-array matrix of biocompatible microcells, one or more conduits, filters, and an oxygen source configured to apply oxygen to the wound. In embodiments the wound dressing comprising a multi-array matrix of biocompatible microcells is placed inside the wound bed then covered with a flexible membrane, for example a polymeric or elastomeric film. In certain embodiments the wound can be imaged such as in three dimensions (height, width, and depth) and the resulting information used to produce a wound dressing custom fit to the particular wound. In certain embodiments the wound management system comprises a pliable cover material that "seals" the wound bed to provide an air-tight seal. In embodiments the conduit providing the oxygen to the wound enters the wound under the dressing or through a slit in the pliable cover material.

In an embodiment, pure oxygen is administered for 90 minutes once a day for four days, followed by a three-day rest period. This cycle can be repeated for as long as the wound appears to be healing. For example in an embodiment pure oxygen can be applied for 20 minutes, or 30 minutes, or 40 minutes, or 50 minutes, or 60 minutes, or 70 minutes, or 80 minutes, or 90 minutes, or 100 minutes, or 110 minutes, or 120 minutes, or 130 minutes, or 140 minutes, or 150 minutes or more, or the like. This can be repeated multiple times in a day, for example oxygen can be administered twice a day, or three times a day, or four times a day, or five times a day, or more, or the like. The therapy can be continued for 1 day, or 2 days, or 3 days, or 4 days, or 5 days, or 6 days, or 7 days, or 8 days, or 9 days, or 10 days, or 11 days, or 12 days, or 13 days, or 14 days, or 15 days, or 16 days, or 17 days, or 18 days, or 19 days, or 20 days or more, or the like.

In certain embodiments the TOT can comprise rest periods between days of oxygen administration. For example a rest period can be 1 day, or 2 days, or 3 days, or 4 days, or 5 days, or 6 days, or 7 days, or 8 days, or 9 days, or 10 days, or 11 days, or 12 days, or 13 days, or 14 days, or 15 days, or 16 days, or 17 days, or 18 days, or 19 days, or 20 days or more, or the like.

In certain embodiments, HBOT can be used to assist with the healing of wounds. For example in some embodiments wounds are treated by using a HBOT wound therapy system comprising a wound management system comprising a dressing comprising a multi-array matrix of biocompatible microcells and an oxygen source configured to apply oxygen to a pressure chamber. In certain embodiments the wound can be imaged such as in three dimensions (height, width, and depth) and the resulting information used to produce a wound dressing custom fit to the particular wound. The imaging can be also used to gauge wound healing.

In an embodiment oxygen is administered for 90 minutes once a day for four days, followed by a three-day rest period. In embodiments patients breathe 100% oxygen most of the time to maximise the effectiveness of their treatment but have periodic "air breaks" during which they breathe room air (21% oxygen) to minimize the risk of oxygen toxicity. This cycle can be repeated for as long as the wound appeared to be healing. For example, in an embodiment pure oxygen can be applied for 20 minutes, or 30 minutes, or 40 minutes, or 50 minutes, or 60 minutes, or 70 minutes, or 80 minutes, or 90 minutes, or 100 minutes, or 110 minutes, or 120 minutes, or 130 minutes, or 140 minutes, or 150 minutes, or more, or the like. This can be repeated multiple times in a day, for example oxygen can be administered twice a day, or three times a day, or four times a day, or five times a day, or more, or the like. The therapy can be continued for 1 day, or 2 days, or 3 days, or 4 days, or 5 days, or 6 days, or 7 days, or 8 days, or 9 days, or 10 days, or 11 days, or 12 days, or 13 days, or 14 days, or 15 days, or 16 days, or 17 days, or 18 days, or 19 days, or 20 days, or more, or the like.

In certain embodiments the HBOT can comprise rest periods between days of oxygen administration. For example a rest period can be 1 day, or 2 days, or 3 days, or 4 days, or 5 days, or 6 days, or 7 days, or 8 days, or 9 days, or 10 days, or 11 days, or 12 days, or 13 days, or 14 days, or 15 days, or 16 days, or 17 days, or 18 days, or 19 days, or 20 days, or more, or the like.

Certain embodiments employ MLCT in combination with a wound management system comprising a wound dressing comprising a multi-array matrix of biocompatible microcells. For example the wound dressing can comprise a compression bandage, for example a short stretch compression bandage, a long stretch compression bandage, a combination thereof, or the like. Short stretch compression bandages are typically applied to a limb (often for treatment of lymphedema or venous ulcers). This type of bandage is capable of shortening around the limb after application and is therefore not exerting ever-increasing pressure during inactivity. This dynamic is called resting pressure and is considered safe and comfortable for long-term treatment. Conversely the stability of the bandage creates a very high resistance to stretch when pressure is applied through internal muscle contraction and joint movement. This force is called working pressure. Long stretch compression bandages usually have long stretch properties meaning their high compressive power can be easily adjusted. Embodiments disclosed herein provide a method of treating wounds using MLCT wherein the innermost layer of the compression system comprises a multi-array matrix of biocompatible microcells.

Embodiments provide a method of promoting the healing of skin grafts. Following attachment of the graft. the graft is covered with a wound management system comprising a wound dressing comprising a multi-array matrix of biocompatible microcells. The method can further comprise NPWT, TOT, or HBOT to promote healing of the skin graft. In embodiments, the skin graft can be autologous wherein the donor skin is taken from a different site on the same individual's body (also known as an autograft). The graft can also be isogeneic wherein the donor and recipient individuals are genetically identical (e.g., monozygotic twins, animals of a single inbred strain; isograft or syngraft). In embodiments the graft can be allogeneic wherein the donor and recipient are of the same species. In further embodiments the graft can be xenogeneic wherein the donor and recipient are of different species (e.g., bovine cartilage; xenograft or heterograft). In certain embodiments the skin graft can be a prosthetic wherein lost tissue is replaced with synthetic materials such as engineered skin substitutes.

Certain embodiments include wound management systems comprising dressings or bandages designed to be used on irregular, non-planar, or "stretching" surfaces, such as joints. A wound management system disclosed herein can include a discontinuous region such as to allow it to stretch after application to a wound or prior to application to a wound to shield a wound from physical stress. Stretching the wound management system prior to application to the wound can allow the system to "pull" the wound edges together after the system is applied. In certain embodiments the wound management system comprising discontinuous regions is applied without prior stretching, such as to allow stretching of the system in response to movement around the wound site. This can be advantageous during the rehabilitation process. For example, continuous passive motion (CPM) is often used during the first phase of rehabilitation following a soft tissue surgical procedure or trauma. CPM can be carried out by a CPM device, which constantly moves the joint through a controlled range of motion; the exact range is dependent upon the joint, but in most cases the range of motion is increased over time. CPM can be used following various types of reconstructive joint surgery such as knee replacement and ACL reconstruction. Embodiments disclosed herein can be used with numerous joints of the body, including, for example, the jaw, the shoulder, the elbow, the wrist, the finger joints, the hip, the knee, the ankle, the toe joints, etc.

Additional embodiments disclosed herein can be used in areas where tissue is prone to movement such as the eyelid, the ear, the lips, the nose, genitalia, etc.

Aspects of the present specification disclose a method of treating an individual with a wound. In embodiments a wound can be a laceration, an abrasion, an avulsion, or the like. Lacerations typically involve tissue that is cut or torn. To treat a laceration tissue can be first cleansed of any blood and foreign material, débrided and irrigated. Local anesthetic can be administered and an atraumatic technique of wound closure can be employed, where wound margins are realigned with careful regard to prevention of any further crush injury to tissues. Wound managements systems can be applied and immobilization is recommended for complex extremity wounds. Abrasions typically involve the removal of a superficial layer of tissue as seen with $1^{st}$ degree burns. The wound can be cleansed of any foreign material, sometimes employing a scrub brush to prevent traumatic tattooing by dirt and gravel. Local anesthetic can be used for pain however treatment of the wound is usually non-surgical, using wound management systems and a topical antibiotic to protect the wound and aid healing. Avulsions are injuries where a section of tissue is torn off either partially or in total. In partial avulsions, the tissue is elevated but remains attached to the body. A total avulsion means that the tissue is completely torn from the body with no point of attachment. In the case of a partial avulsion where the torn tissue is still well-vascularized and viable, the tissue can be gently cleansed and irrigated and the flap can be reattached to its anatomical position with a few sutures. If the torn tissue is non-viable it is often excised and the wound closed using a skin graft or local flap. In the case of a total avulsion the tissue is often very thick and demands debulking and defattening methods before it can be regrafted. Major avulsions describe amputation of extremities, fingers, ears, nose, scalp or eyelids.

Treatment of Bites

Systems disclosed herein can be used to treat animal bites, for example snake bites. A LLMC or LLEF system can be applied to the bite(s) or bitten area, wherein the low level micro-current or electric field can neutralize the immune reaction to the bites or the venom, or neutralize the antigens present in such bites and thus reduce pain and itching. In embodiments the systems and devices disclosed herein can treat venomous bites by altering the function of venoms, such as, for example, protein-based venoms.

Systems disclosed herein can be used to treat insect bites, for example mosquito bites. A LLMC or LLEF system can be applied to the bite(s) or bitten area, wherein the low level micro-current or electric field can neutralize the immune reaction to the bites or any venom and thus reduce pain and itching.

Treatment of Microbial Infection

Embodiments of the disclosed LLMC and LLEF systems can provide microbicidal activity. For example, embodiments disclosed herein can prevent, limit, or reduce formation of biofilms by interfering with bacterial signaling. Further embodiments can kill bacteria through an established biofilm.

Embodiments of the disclosed LLMC and LLEF systems can provide microbicidal activity. For example, embodiments disclosed herein can prevent, limit, or reduce formation of biofilms by interfering with bacterial signaling. Further embodiments can kill bacteria through an established biofilm.

Aspects disclosed herein include systems, devices, and methods for treating parasitic infections. For example, methods disclosed herein include treatments for ectoparasitic infections caused by, for example, *Sarcoptes scabiei* (causes scabies), *Pediculus humanus capitis* (causes head lice), *Phthirus pubis* (causes pubic lice), *Leishmania* (causes leishmaniasis), and the like. Leishmaniasis is a highly focal disease with widely scattered foci. The parasite may survive for decades in asymptomatic infected people, who are of great importance for the transmission since they can spread visceral leishmaniasis indirectly through the sandflies. The parasites can also be transmitted directly from person to person through the sharing of infected needles which is often the case with the *Leishmania*/HIV co-infection. Cutaneous leishmaniasis is the most common form, which causes a sore at the bite site, which heals in a few months to a year, leaving an unpleasant-looking scar. Systems disclosed herein can be used to treat cutaneous leishmaniasis in the initial infection stage as well as the latent stage or in the active disfiguring lesions resulting from the infection.

Cellular Activation

Embodiments of the disclosed LLMC and LLEF systems can increase cell migration by applying an electric current or electric field or both to a treatment area. For example, the systems can increase migration of human keratinocytes. The systems can also be used to promote re-epithelialization for example in a wound.

Embodiments of the disclosed LLMC and LLEF systems can increase glucose uptake in target tissues and cells, for example by applying a LLEF system disclosed herein to a treatment area where increased uptake of glucose is desired. In embodiments glucose uptake can be increased to energize mitochondria.

Embodiments of the disclosed LLMC and LLEF systems can increase cell signaling in target tissues and cells, for example by applying a LLEF system disclosed herein to a treatment area where increased cell signaling is desired.

Embodiments of the disclosed LLMC and LLEF systems can create hydrogen peroxide in target tissues and cells, for example by applying a LLEF system disclosed herein to a treatment area where hydrogen peroxide production is desired.

Treatment of Disease

Embodiments of the disclosed LLMC and LLEF systems can be used to treat disease. For example, embodiments can be used to increase glucose uptake thus reducing serum glucose levels and treating diseases relating to increased glucose levels, such as diabetes. Increasing cellular uptake of glucose can also have a limiting effect on glucose level variations (excursions), thus treating both hyper- and hypoglycemia. In embodiments, methods of treating glucose-related diseases can comprise applying systems to a patient in need thereof. For example, LLEF or LLMC systems can be applied to a patient's skin, or applied using a catheter, or applied using a pharmaceutical composition. A pharmaceutical composition disclosed herein can be administered to an individual using a variety of routes. Routes of administration suitable for use as disclosed herein include both local and systemic administration. Local administration results in significantly more delivery of a composition to a specific location as compared to the entire body of the individual, whereas, systemic administration results in delivery of a composition to essentially the entire body of the individual.

Muscle Regeneration

Embodiments of the disclosed LLMC and LLEF systems can be used to regenerate muscle tissue. For example, embodiments can be used to direct macrophage migration to damaged or wounded muscle thus helping to regenerate the muscle.

EXAMPLES

The following non-limiting examples are provided for illustrative purposes only in order to facilitate a more complete understanding of representative embodiments. These examples should not be construed to limit any of the embodiments described in the present specification including those pertaining to the methods of treating wounds.

Example 1

Cell Migration Assay

The in vitro scratch assay is an easy, low-cost and well-developed method to measure cell migration in vitro. The basic steps involve creating a "scratch" in a cell monolayer, capturing images at the beginning and at regular intervals during cell migration to close the scratch, and comparing the images to quantify the migration rate of the cells. Compared to other methods, the in vitro scratch assay is particularly suitable for studies on the effects of cell-matrix and cell-cell interactions on cell migration, mimic cell migration during wound healing in vivo and are compatible with imaging of live cells during migration to monitor intracellular events if desired. In addition to monitoring migration of homogenous cell populations, this method has also been adopted to measure migration of individual cells in the leading edge of the scratch. Not taking into account the time for transfection of cells, in vitro scratch assay per se usually takes from several hours to overnight.

Human keratinocytes were plated under plated under placebo or a LLMC system (labeled "PROCELLERA®"). Cells were also plated under silver-only or zinc-only dressings. After 24 hours, the scratch assay was performed. Cells plated under the PROCELLERA® device displayed increased migration into the "scratched" area as compared to any of the zinc, silver, or placebo dressings. After 9 hours, the cells plated under the PROCELLERA® device had almost "closed" the scratch. This demonstrates the importance of electrical activity to cell migration and infiltration.

In addition to the scratch test, genetic expression was tested. Increased insulin growth factor (IGF)-1R phosphorylation was demonstrated by the cells plated under the PROCELLERA® device as compared to cells plated under insulin growth factor alone.

Integrin accumulation also affects cell migration. An increase in integrin accumulation was achieved with the LLMC system. Integrin is necessary for cell migration, and is found on the leading edge of migrating cell.

Thus, the tested LLMC system enhanced cellular migration and IGF-1R/integrin involvement. This involvement demonstrates the effect that the LLMC system had upon cell receptors involved with the wound healing process.

Example 2

Zone of Inhibition Test

For cellular repair to be most efficient, available energy should not be shared with ubiquitous microbes. In this "zone of inhibition" test, placebo, a LLMC device (PROCELLERA®) and silver only were tested in an agar medium with a 24 hour growth of organisms. Bacteria grew over the placebo, there was a zone of inhibition over the PROCELLERA® and a minimal inhibition zone over the silver. Because the samples were "buried" in agar, the electricidal effect of the LLMC system could be tested. This could mean the microbes were affected by the electrical field or the silver ion transport through the agar was enhanced in the presence of the electric field. Silver ion diffusion, the method used by silver based antimicrobials, alone was not sufficient. The test demonstrates the improved bactericidal effect of PROCELLERA® as compared to silver alone.

Example 3

Wound Care Study

The medical histories of patients who received "standard-of-care" wound treatment ("SOC"; n=20), or treatment with a LLMC device as disclosed herein (n=18), were reviewed. The wound care device used in the present study consisted of a discrete matrix of silver and zinc dots. A sustained voltage of approximately 0.8 V was generated between the dots. The electric field generated at the device surface was measured to be 0.2-1.0 V, 10-50 µA.

Wounds were assessed until closed or healed. The number of days to wound closure and the rate of wound volume reduction were compared. Patients treated with LLMC received one application of the device each week, or more frequently in the presence of excessive wound exudate, in conjunction with appropriate wound care management. The LLMC was kept moist by saturating with normal saline or conductive hydrogel. Adjunctive therapies (such as negative pressure wound therapy [NPWT], etc.) were administered with SOC or with the use of LLMC unless contraindicated. The SOC group received the standard of care appropriate to the wound, for example antimicrobial dressings, barrier creams, alginates, silver dressings, absorptive foam dressings, hydrogel, enzymatic debridement ointment, NPWT, etc. Etiology-specific care was administered on a case-by-case basis. Dressings were applied at weekly intervals or more. The SOC and LLMC groups did not differ significantly in gender, age, wound types or the length, width, and area of their wounds.

Wound dimensions were recorded at the beginning of the treatment, as well as interim and final patient visits. Wound dimensions, including length (L), width (W) and depth (D) were measured, with depth measured at the deepest point. Wound closure progression was also documented through digital photography. Determining the area of the wound was performed using the length and width measurements of the wound surface area.

Closure was defined as 100% epithelialization with visible effacement of the wound. Wounds were assessed 1 week post-closure to ensure continued progress toward healing during its maturation and remodeling phase.

Wound types included in this study were diverse in etiology and dimensions, thus the time to heal for wounds was distributed over a wide range (9-124 days for SOC, and 3-44 days for the LLMC group). Additionally, the patients often had multiple co-morbidities, including diabetes, renal disease, and hypertension. The average number of days to wound closure was 36.25 (SD=28.89) for the SOC group and 19.78 (SD=14.45) for the LLMC group, p=0.036. On average, the wounds in the LLMC treatment group attained closure 45.43% earlier than those in the SOC group.

Based on the volume calculated, some wounds improved persistently while others first increased in size before improving. The SOC and the LLMC groups were compared to each other in terms of the number of instances when the dimensions of the patient wounds increased (i.e., wound treatment outcome degraded). In the SOC group, 10 wounds (50% for n=20) became larger during at least one measurement interval, whereas 3 wounds (16.7% for n=18) became larger in the LLMC group (p=0.018). Overall, wounds in both groups responded positively. Response to treatment was observed to be slower during the initial phase, but was observed to improve as time progressed.

The LLMC wound treatment group demonstrated on average a 45.4% faster closure rate as compared to the SOC group. Wounds receiving SOC were more likely to follow a "waxing-and-waning" progression in wound closure compared to wounds in the LLMC treatment group.

Compared to localized SOC treatments for wounds, the LLMC (1) reduces wound closure time, (2) has a steeper wound closure trajectory, and (3) has a more robust wound healing trend with fewer incidence of increased wound dimensions during the course of healing.

Example 4

LLMC Influence on Human Keratinocyte Migration

An LLMC-generated electrical field was mapped, leading to the observation that LLMC generates hydrogen peroxide, known to drive redox signaling. LLMC-induced phosphorylation of redox-sensitive IGF-1R was directly implicated in cell migration. The LLMC also increased keratinocyte mitochondrial membrane potential.

The LLMC was made of polyester printed with dissimilar elemental metals. It comprises alternating circular regions of silver and zinc dots, along with a proprietary, biocompatible binder added to lock the electrodes to the surface of a flexible substrate in a pattern of discrete reservoirs. When the LLMC contacts an aqueous solution, the silver positive electrode (cathode) is reduced while the zinc negative electrode (anode) is oxidized. The LLMC used herein consisted of metals placed in proximity of about 1 mm to each other thus forming a redox couple and generating an ideal potential on the order of 1 Volt. The calculated values of the electric field from the LLMC were consistent with the magnitudes that are typically applied (1-10 V/cm) in classical electrotaxis experiments, suggesting that cell migration observed with the bioelectric dressing is likely due to electrotaxis.

Measurement of the potential difference between adjacent zinc and silver dots when the LLMC is in contact with de-ionized water yielded a value of about 0.2 Volts. Though the potential difference between zinc and silver dots can be measured, non-intrusive measurement of the electric field arising from contact between the LLMC and liquid medium was difficult. Keratinocyte migration was accelerated by exposure to an Ag/Zn LLMC. Replacing the Ag/Zn redox couple with Ag or Zn alone did not reproduce the effect of keratinocyte acceleration.

Exposing keratinocytes to an LLMC for 24 h significantly increased green fluorescence in the dichlorofluorescein (DCF) assay indicating generation of reactive oxygen species under the effect of the LLMC. To determine whether $H_2O_2$ is generated specifically, keratinocytes were cultured with a LLMC or placebo for 24 h and then loaded with PF6-AM (Peroxyfluor-6 acetoxymethyl ester; an indicator of endogenous $H_2O_2$). Greater intracellular fluorescence was observed in the LLMC keratinocytes compared to the cells grown with placebo. Over-expression of catalase (an enzyme that breaks down $H_2O_2$) attenuated the increased migration triggered by the LLMC. Treating keratinocytes with N-Acetyl Cysteine (which blocks oxidant-induced signaling) also failed to reproduce the increased migration observed with LLMC. Thus, $H_2O_2$ signaling mediated the increase of keratinocyte migration under the effect of the electrical stimulus.

External electrical stimulus can up-regulate the TCA (tricarboxylic acid) cycle. The stimulated TCA cycle is then expected to generate more NADH and $FADH_2$ to enter into the electron transport chain and elevate the mitochondrial membrane potential ($\Delta m$). Fluorescent dyes JC-1 and TMRM were used to measure mitochondrial membrane potential. JC-1 is a lipophilic dye which produces a red fluorescence with high $\Delta m$ and green fluorescence when $\Delta m$ is low. TMRM produces a red fluorescence proportional to $\Delta m$. Treatment of keratinocytes with LLMC for 24 h demonstrated significantly high red fluorescence with both JC-1 and TMRM, indicating an increase in mitochondrial membrane potential and energized mitochondria under the effect of the LLMC. As a potential consequence of a stimulated TCA cycle, available pyruvate (the primary substrate for the TCA cycle) is depleted resulting in an enhanced rate of glycolysis. This can lead to an increase in glucose uptake in order to push the glycolytic pathway forward. The rate of glucose uptake in HaCaT cells treated with LLMC was examined next. More than two fold enhancement of basal glucose uptake was observed after treatment with LLMC for 24 h as compared to placebo control.

Keratinocyte migration is known to involve phosphorylation of a number of receptor tyrosine kinases (RTKs). To determine which RTKs are activated as a result of LLMC, scratch assay was performed on keratinocytes treated with LLMC or placebo for 24 h. Samples were collected after 3 h and an antibody array that allows simultaneous assessment of the phosphorylation status of 42 RTKs was used to quantify RTK phosphorylation. It was determined that LLMC significantly induces IGF-1R phosphorylation. Sandwich ELISA using an antibody against phospho-IGF-1R and total IGF-1R verified this determination. As observed with the RTK array screening, potent induction in phosphorylation of IGF-1R was observed 3 h post scratch under the influence of LLMC. IGF-1R inhibitor attenuated the increased keratinocyte migration observed with LLMC treatment.

MBB (monobromobimane) alkylates thiol groups, displacing the bromine and adding a fluorescent tag (lamda emission=478 nm). MCB (monochlorobimane) reacts with only low molecular weight thiols such as glutathione. Fluorescence emission from UV laser-excited keratinocytes loaded with either MBB or MCB was determined for 30 min. Mean fluorescence collected from 10,000 cells showed a significant shift of MBB fluorescence emission from cells. No significant change in MCB fluorescence was observed, indicating a change in total protein thiol but not glutathione. HaCaT cells were treated with LLMC for 24 h followed by a scratch assay. Integrin expression was observed by immuno-cytochemistry at different time points. Higher integrin expression was observed 6 h post scratch at the migrating edge.

Consistent with evidence that cell migration requires $H_2O_2$ sensing, we determined that by blocking $H_2O_2$ signaling by decomposition of $H_2O_2$ by catalase or ROS scavenger, N-acetyl cysteine, the increase in LLMC-driven cell migration is prevented. The observation that the LLMC increases $H_2O_2$ production is significant because in addition to cell migration, hydrogen peroxide generated in the wound margin tissue is required to recruit neutrophils and other leukocytes to the wound, regulates monocyte function, and VEGF signaling pathway and tissue vascularization. Therefore, external electrical stimulation can be used as an effective strategy to deliver low levels of hydrogen peroxide over time to mimic the environment of the healing wound and thus should help improve wound outcomes. Another phenomenon observed during re-epithelialization is increased expression of the integrin subunit $\alpha v$. There is evidence that integrin, a major extracellular matrix receptor, polarizes in response to applied ES and thus controls directional cell migration. It may be noted that there are a number of integrin subunits, however we chose integrin $\alpha v$ because of evidence of association of $\alpha v$ integrin with IGF-1R, modulation of IGF-1 receptor signaling, and of driving keratinocyte locomotion. Additionally, integrin$_{\alpha v}$ has been reported to contain vicinal thiols that provide site for redox activation of function of these integrins and therefore the increase in protein thiols that we observe under the effect of ES may be the driving force behind increased integrin mediated cell migration. Other possible integrins which may be playing a role in LLMC-induced IGF-1R mediated keratinocyte migration are $\alpha 5$ integrin and $\alpha 6$ integrin.

Materials and Methods

Cell culture—Immortalized HaCaT human keratinocytes were grown in Dulbecco's low-glucose modified Eagle's medium (Life Technologies, Gaithersburg, Md., U.S.A.) supplemented with 10% fetal bovine serum, 100 U/ml penicillin, and 100 µg/ml streptomycin. The cells were maintained in a standard culture incubator with humidified air containing 5% $CO_2$ at 37° C.

Scratch assay—A cell migration assay was performed using culture inserts (IBIDI®, Verona, Wis.) according to the manufacturers instructions. Cell migration was measured using time-lapse phase-contrast microscopy following withdrawal of the insert. Images were analyzed using the AxioVision Rel 4.8 software.

N-Acetyl Cysteine Treatment—Cells were pretreated with 5 mM of the thiol antioxidant N-acetylcysteine (Sigma) for 1 h before start of the scratch assay.

IGF-1R inhibition—When applicable, cells were preincubated with 50 nM IGF-1R inhibitor, picropodophyllin (Calbiochem, MA) just prior to the Scratch Assay.

Cellular $H_2O_2$ Analysis—To determine intracellular $H_2O_2$ levels, HaCaT cells were incubated with 5 pM PF6-AM in PBS for 20 min at room temperature. After loading, cells were washed twice to remove excess dye and visualized using a Zeiss Axiovert 200M microscope.

Catalase gene delivery—HaCaT cells were transfected with $2.3 \times 10^7$ pfu AdCatalase or with the empty vector as control in 750 μL of media. Subsequently, 750 μL of additional media was added 4 h later and the cells were incubated for 72 h.

RTK Phosphorylation Assay—Human Phospho-Receptor Tyrosine Kinase phosphorylation was measured using Phospho-RTK Array kit (R & D Systems).

ELISA—Phosphorylated and total IGF-1R were measured using a DuoSet IC ELISA kit from R&D Systems.

Determination of Mitochondrial Membrane Potential—Mitochondrial membrane potential was measured in HaCaT cells exposed to the LLMC or placebo using TMRM or JC-1 (MitoProbe JC-1 Assay Kit for Flow Cytometry, Life Technologies), per manufacturers instructions for flow cytometry.

Integrin αV Expression—Human HaCaT cells were grown under the MCD or placebo and harvested 6 h after removing the IBIDI® insert. Staining was done using antibody against integrin αV (Abcam, Cambridge, Mass.).

Example 5

Generation of Superoxide

A LLMC system was tested to determine the effects on superoxide levels which can activate signal pathways. PROCELLERA® LLMC system increased cellular protein sulfhydryl levels. Further, the PROCELLERA® system increased cellular glucose uptake in human keratinocytes. Increased glucose uptake can result in greater mitochondrial activity and thus increased glucose utilization, providing more energy for cellular migration and proliferation. This can speed wound healing.

Example 6

Treating a Knee Laceration with NPWT

A 17 year-old boy injures his knee playing football. The emergency room doctor cleans the wound then applies a wound management system as described herein. The doctor also prescribes NPWT to assist in healing the wound. The wound is digitally imaged and from the imaging data a custom-fit wound management system is prepared. The wound dressing with a surface comprising a multi-array matrix of biocompatible microcells fits inside the wound bed and extends beyond the perimeter of the wound by at least 1 cm. Negative pressure at a continuous 15 mmHg is applied for an hour a day for 5 days, then repeated after a rest period of 2 days. The cycle is repeated for a month, after which the knee has healed with very little visible scarring.

Example 7

Treating a Diabetic Ulcer with MLCT

A 58 year-old male with a history of diabetes has ulcers on his legs. All other treatment modalities have failed to heal the ulcers. A wound management system comprising a multi-array matrix of biocompatible microcells is applied over the ulcer as a component in a MLCT therapy protocol. Healing initiation is observed within weeks and the ulcers are fully closed within 5 months.

Example 8

Treating an Abrasion with Synthetic Skin

A 47 year-old female severely abrades her arms in an automobile accident. Synthetic skin is applied to the abraded tissue, which is then covered with wound management systems as described herein, including embodiments with discontinuous regions to allow for joint movement. The injuries heal without the need for skin grafts.

Example 9

Treatment of a Full-Thickness Wound with TOT

A 35-year old male suffers from a burn to his shoulder. The burn is excised, then digitally imaged to capture the precise topography of the wound. A pliable wound management system that exactly matches the wound topography is produced, the system comprising a bioelectric antimicrobial device containing a multi-array matrix of biocompatible microcells. The system is used to cover the wound. Topical oxygen is applied to the wound for an hour a day for three days. The burn heals without the need for skin grafts.

Example 10

Treatment of a Surgical Site with HBOT

A 56-year old female suffering from squamous cell carcinoma undergoes a procedure to remove a tumor. The tumor removal sites are covered with breathable wound management systems comprising a multi-array matrix of biocompatible microcells. The patient then undergoes three cycles of HBOT, each cycle including 90 minutes of therapy each day for 4 days, followed by 2 "rest" days. The surgical site heals with minimal scarring.

Example 11

Treatment of Open Fracture with NPWT

A 7-year old male suffers a grade-III open tibia-fibula fracture, leaving exposed bone and muscle. The wound is dressed with wound management systems s as described herein comprising a bioelectric antimicrobial material containing a multi-array matrix of biocompatible microcells. The boy also undergoes a NPWT regime consisting of 60 minutes of negative pressure (at 12 mmHg) three times a week. The wound heals without the need of muscle or skin grafts. The wound is also kept free from microbial contamination as a result of the broad-spectrum antimicrobial effect of the wound management systems disclosed herein.

Example 12

Treatment of a Surgical Site

A 25-year old male suffers a tear of his medial collateral ligament (MCL) while surfing. Following surgery to repair the MCL, wound management systems comprising a bioelectric antimicrobial device containing a multi-array matrix of biocompatible microcells, including embodiments with discontinuous regions to allow for joint movement, are applied to the site of the surgery. The wound is also kept free from microbial contamination as a result of the broad-spectrum antimicrobial effect of the wound dressings. Continuous passive motion (CPM) is employed to constantly move the joint through a controlled range of motion. The patient recovers fully with no limitations on his physical capabilities.

Example 13

Treatment of a Burn with Synthetic Skin

A 25-year old male suffers severe burns to his upper abdomen. Synthetic skin grafts are applied to the burned areas. The grafts are then covered with wound management systems comprising a wound dressing comprising a bioelectric antimicrobial device containing a multi-array matrix of biocompatible microcells. Over the next 8 weeks the grafts heal. The grafts are also kept free from microbial contamination as a result of the broad-spectrum antimicrobial effect of the wound dressings disclosed herein.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, including the best mode known to the inventor for carrying out the methods and devices described herein. Of course, variations on these described embodiments will become apparent to those of ordinary skill in the art upon reading the foregoing description. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

The invention claimed is:

1. A system for treating a wound comprising;
   a device for providing adjunctive wound therapy, said therapy comprising Hyperbaric Oxygen Therapy (HBOT) or Topical Oxygen Therapy (TOT); and
   a substrate comprising biocompatible electrodes comprising a first array comprising a pattern of microcells formed from a first conductive material, and a second array comprising a pattern of microcells formed from a second conductive material, wherein said electrodes are capable of generating at least one of a Low Level Electric Field (LLEF), or when said first and second arrays are introduced to an electrolytic solution, a Low Level Micro Current (LLMC) of between 1 and 200 micro-amperes.

2. The system of claim 1 wherein the first conductive material and the second conductive material comprise the same material.

3. The system of claim 2 wherein the first and second array each comprise a discrete circuit.

4. The system of claim 3, further comprising a power source.

5. The system of claim 1 wherein the first array and the second array spontaneously generate a LLEF.

6. The system of claim 1 wherein the LLMC is between 1 and 100 micro-amperes.

7. The system of claim 1 wherein the LLMC is between 100 and 200 micro-amperes.

8. The system of claim 7 wherein the LLMC is between 150 and 200 micro-amperes.

9. A method for treating a wound comprising securing a wound dressing in a sealed environment adjacent the wound and applying HBOT or TOT in the sealed environment, wherein the wound dressing comprises a pliable dressing material comprising on its surface a multi-array matrix of biocompatible microcells, said matrix comprising:
   a first array forming a pattern of microcells formed from a first conductive material, and
   a second array forming a pattern of microcells formed from a second conductive material, such conductive material capable of defining at least one voltaic cell for spontaneously generating at least one electrical current with the metal species of the first array when said first and second arrays are electrically connected an electrolytic solution, wherein said electric current is between 1 and 200 micro-amperes.

10. The method of claim 9 wherein the method for treating a wound comprises applying HBOT.

11. The method of claim 9 wherein the method for treating a wound comprises applying TOT.

12. The method of claim 9 wherein the electric current is between 50 and 150 micro-amperes.

13. The method of claim 9 wherein the electric current is between 1 and 100 micro-amperes.

14. The method of claim 9 wherein the electric current is between 100 and 200 micro-amperes.

* * * * *